(12) United States Patent
Pulido et al.

(10) Patent No.: US 9,517,258 B2
(45) Date of Patent: Dec. 13, 2016

(54) METHODS AND MATERIALS FOR TREATING CANCER

(71) Applicants: Mayo Foundation for Medical Education and Research, Rochester, MN (US); University of Leeds, Leeds (GB)

(72) Inventors: Jose S. Pulido, Rochester, MN (US); Richard G. Vile, Rochester, MN (US); Timothy J. Kottke, Oronoco, MN (US); Alan A. Melcher, Roundhay (GB); Peter Selby, Roundhay (GB)

(73) Assignees: Mayo Foundation for Medical Education and Research, Rochester, MN (US); University of Leeds, Leeds (GB)

( * ) Notice: Subject to any disclaimer, the term of this patent is extended or adjusted under 35 U.S.C. 154(b) by 0 days.

(21) Appl. No.: 14/385,240

(22) PCT Filed: Mar. 15, 2013

(86) PCT No.: PCT/US2013/031953
§ 371 (c)(1),
(2) Date: Sep. 15, 2014

(87) PCT Pub. No.: WO2013/138697
PCT Pub. Date: Sep. 19, 2013

(65) Prior Publication Data
US 2015/0064218 A1  Mar. 5, 2015

Related U.S. Application Data

(60) Provisional application No. 61/611,387, filed on Mar. 15, 2012.

(51) Int. Cl.
| | | |
|---|---|---|
| *C12N 15/10* | (2006.01) | |
| *A61K 39/00* | (2006.01) | |
| *A61K 31/7088* | (2006.01) | |
| *C12Q 1/68* | (2006.01) | |
| *A61K 48/00* | (2006.01) | |

(52) U.S. Cl.
CPC ....... *A61K 39/0011* (2013.01); *A61K 31/7088* (2013.01); *C12N 15/1086* (2013.01); *C12Q 1/6876* (2013.01); *A61K 48/00* (2013.01); *A61K 2039/53* (2013.01); *C12Q 2600/106* (2013.01)

(58) Field of Classification Search
CPC .......... A61K 39/0011; C12N 15/1086
See application file for complete search history.

(56) References Cited

U.S. PATENT DOCUMENTS

| | | | |
|---|---|---|---|
| 5,695,963 A | 12/1997 | McKnight et al. | |
| 6,140,053 A | 10/2000 | Koster | |
| 2010/0168206 A1 | 7/2010 | Gollob et al. | |
| 2012/0258046 A1 | 10/2012 | Mutzke | |
| 2012/0308484 A1 | 12/2012 | Szalay et al. | |
| 2012/0308601 A1 | 12/2012 | Vile et al. | |
| 2013/0287772 A1 | 10/2013 | Halbert et al. | |

FOREIGN PATENT DOCUMENTS

| | | |
|---|---|---|
| WO | WO 2008/109825 | 9/2008 |
| WO | WO 2011/100468 | 8/2011 |
| WO | WO 2013/138697 | 9/2013 |
| WO | WO 2013/173223 | 11/2013 |
| WO | WO 2013/178344 | 12/2013 |

OTHER PUBLICATIONS

Heim, S. Normal high resolution karyotypes in patients with adenomatosis of the colon and rectum. Hereditas, vol. 102, pp. 171-175, 1985.*
European Search Report for Application No. 13760532.5, dated Oct. 20, 2015, 14 pages.
Vinals et al., "Using in silico transcriptomics to search for tumor-associated antigens for immunotherapy," Vaccine, 19 (17-19)2607-2614, Mar. 21, 2001.
Office Action for U.S. Appl. No. 13/578,224 mailed Sep. 24, 2015, 16 pages.
Office Action for U.S. Appl. No. 13/578,224 mailed Jun. 5, 2015, 14 pages.
Office Action for U.S. Appl. No. 13/578,224 mailed Dec. 4, 2014, 14 pages.
Office Action for U.S. Appl. No. 13/578,224 mailed Dec. 27, 2013, 17 pages.
Office Action for U.S. Appl. No. 13/578,224 mailed May 8, 2013, 14 pages.
"A Randomized Study of Nivolumab Versus Bevacizumab and a Safety Study of Nivolumab in Adult Subjects With Recurrent Glioblastoma (GBM) (CheckMate 143)," Clinical Trials.gov [online] Dec. 2014, [retrieved on Mar. 18, 2015]. Retrieved from the Internet: <URL: https://clinicaltrials.gov/ct2/show/NCT02017717>, 3 pages.
"UniProt entry P08183—MDR1_HUMAN: Multidrug resistance protein 1," Aug. 1, 1988, pp. 1-12. Retrieved from the Internet: <http://www.uniprot.org/uniprot/P08183#pathology_and_biotech> on Jun. 3, 2015.
"UniProt entry P35968—VGFR2_HUMAN: Vascular endothelial growth factor receptor 2," Jun. 1, 1994, pp. 1-8. Retrieved from the Internet: <http://www.uniprot.org/uniprot/P35968> on Jun. 3, 2015.
"Using Viro/Immunotherapy to Target Stem-Like Cells of Tumor Recurrence," Oncolytic Viruses and Stem Cell Workshop, National Cancer Institute (NCI), Washington D.C., Sep. 6, 2013, [slideshow] 51 pages.

(Continued)

*Primary Examiner* — Jennifer Dunston
(74) *Attorney, Agent, or Firm* — Fish & Richardson P.C.

(57) ABSTRACT

This document provides methods and materials for treating cancer. For example, methods and materials for identifying antigens and combinations of antigens that can be used to treat cancer as well as combinations of antigens having the ability to reduce established tumors within a mammal (e.g., a human) are provided.

13 Claims, 11 Drawing Sheets

(56) References Cited

OTHER PUBLICATIONS

Ahmad et al., "Optimised electroporation mediated DNA vaccination for treatment of prostate cancer," *Genetics Vaccines and Therapy*, 8:1, pp. 1-13, Feb. 5, 2010.

Alonso-Camino et al., "The profile of tumor antigens which can be targeted by immunotherapy depends upon the tumor's anatomical site," *Mol. Ther.*, 22(11):1936-1948, Nov. 2014.

Avogadri and Wolchok., "Selecting antigens for cancer vaccines," Nat. Biotechnol. 30(4):328-329, Apr. 10, 2012.

Barry et al., "Expression library immunization to discover and improve vaccine antigens," *Immunol Rev.*, 199:68-83, Jun. 2004.

Baxevanis et al., "Cancer immunotherapy," *Crit Rev Clin Lab Sci.*, 46(4): 167-189, 2009.

Boisgerault et al., "Functional cloning of recurrence-specific antigens identifies molecular targets to treat tumor relapse," Mol. Ther., 21(8):1507-1516, Epub Jun. 11, 2013.

Bridle et al., "Vesicular stomatitis virus as a novel cancer vaccine vector to prime antitumor immunity amenable to rapid boosting with adenovirus," Mol. Ther., 17(10):1814-1821, Oct. 2009.

Chen et al., "Principal expression of two mRNA isoforms (ABCB 5alpha and ABCB 5beta ) of the ATP-binding cassette transporter gene ABCB 5 in melanoma cells and melanocytes, " *Pigment Cell Res.*, 18(2):102-112, Apr. 2005 [author manuscript].

Cho et al., "A potent vaccination strategy that circumvents lymphodepletion for effective antitumor adoptive T-cell therapy," *Cancer Res.*, 72:1986-1995, Apr. 15, 2012.

Chong et al., "Expression of co-stimulatory molecules by tumor cells decreases tumorigenicity but may also reduce systemic antitumor immunity," *Hum Gene Ther.*, 7(14):1771-1779, Sep. 10, 1996.

Cluff, "Monophosphoryl Lipid A (MPL) as an Adjuvant for Anit-Cancer Vaccines: Clinical Results," *Lipid A in Cancer Therapy*, Landes Bioscience and Springer Science and Business Media, Chpt. 10, pp. 111-123, 2009.

Daniels et al., "A simple method to cure established tumors by inflammatory killing of normal cells," Nature Biol., 22(9):1125-1132, Epub Aug. 2004.

Diaz et al., "Oncolytic immunovirotherapy for melanoma using vesicular stomatitis virus," Cancer Res., 67(6):2840-2848 Mar. 2007.

Ebert et al., "Systemic therapy of experimental breast cancer metastases by mutant vesicular stomatitis virus in immune-competent mice," Cancer Gene Ther., 12(4):350-358, Apr. 2005.

Fernandez et al., "Genetically engineered vesicular stomatitis virus in gene therapy: application for treatment of malignant disease," J. Virol., 76(2):895-904, Jan. 2002.

Ferrone, "Immunotherapy dispenses with tumor antigens," Nature Biotech., 2004, 22(9):1096-1098.

Francisco et al., "Chapter 4: Melanoma Genetics: From Susceptibility to Progression," Melanoma—From Early Detection to Treatment, Dr. Ht Duc (Ed.), pp. 83-136. Retrieved from the Internet: <http://www.intechopen.com/books/melanoma-from-early-detection-to-treatment/melanoma-genetics-from-susceptibility-to-progression> Jan. 2013.

Galivo et al., "Interference of CD40L-mediated tumor immunotherapy by oncolytic vesicular stomatitis virus," Human Gene Ther., 21(4):439-450, Apr. 2010.

Galivo et al., "Single-cycle viral gene expression, rather than progressive replication and oncolysis, is required for VSV therapy of B16 melanoma," Gene Ther., 17(2):158-170, print Feb. 2010, Epub Dec. 2009.

Hall and Brown, "Human N-ras: cDNA cloning and gene structure," Nucleic Acids Res., 13(14):5255-5268, Jul. 1985.

Hogquist et al., "T cell receptor antagonist peptides induce positive selection," Cell, 76(1):17-27, Jan. 1994.

Jenks et al., "Safety studies on intrahepatic or intratumoral injection of oncolytic vesicular stomatitis virus expressing interferon-beta in rodents and nonhuman primates," *Hum. Gene Ther.*, 21(4):451-462, Apr. 2010.

Joseph et al., "Association of the autoimmune disease scleroderma with an immunologic response to cancer," *Science*, 343(6167):152-157, Epub Dec. 5, 2013.

Kaluza et al., "Adoptive transfer of cytotoxic T lymphocytes targeting two different antigen limits antigens loss and tumor escape," *Hum Gene Ther.*, 23(10):1054-1064, Epub Aug. 13, 2012.

Kottke et al, "Broad antigenic coverage induced by vaccination with virus-based cDNA libraries cures established tumors," Nat Med., 17(7):854-859, Jun. 2011.

Kottke et al., "Antitumor immunity can be uncoupled from autoimmunity following heat shock protein 70-mediated inflammatory killing of normal pancreas," Cancer Res., 69(19):7767-1774, Oct. 2009.

Kottke et al., "Induction of hsp70-mediated Th17 autoimmunity can be exploited as immunotherapy for metastatic prostate cancer," Cancer Res., 67(24):11970-11979, Dec. 2007.

Lawson et al., "Recombinant vesicular stomatitis viruses from DNA," *PNAS*, 92(10):4477-4481, May 9, 1995.

Linardakis et al., "Enhancing the efficacy of a weak allogeneic melanoma vaccine by viral fusogenic membrane glycoprotein-mediated tumor cell-tumor cell fusion," Cancer Res., 62(19): 5495-5504, Oct. 2002.

Obuchi et al., "Development of recombinant vesicular stomatitis viruses that exploit defects in host defense to augment specific oncolytic activity," *J. Virol.*, 77(16):8843-8856, Aug. 2003.

Overwijk et al., "Tumor regression and autoimmunity after reversal of a functionally tolerant state of self-reactive CD8+ T cells," J. Exp. Med., 198(4):569-580, Aug. 2003.

Pulido et al., "Using virally expressed melanoma cDNA libraries to identify tumor-associated antigens that cure melanoma," *Nat Biotechnol.*, 30(4):337-343, Mar. 18, 2012.

Radvanyi, "Immunotherapy Exposes Cancer Stem Cell Resistance and a New Synthetic Lethality," Mol. Ther. 21:1472-1474, Aug. 2013.

Ramsburg et al., "A vesicular stomatitis virus recombinant expressing granulocyte-macrophage colony-stimulating factor induces enhanced T-cell responses and is highly attenuated for replication in animals," *J. Virol.*, 79(24):15043-15053, Dec. 2005.

Roda et al., "Stabilization of HIF-2α induces sVEGFR-1 production from tumor-associated macrophages and decreases tumor growth in a murine melanoma model," *J. Immunol.*, 189(6):3168-3177, Sep. 15, 2012

Rommelfanger et al., "Systemic combination virotherapy for melanoma with tumor antigen-expressing vesicular stomatitis virus and adoptive T-cell transfer," *Cancer Res.*, 72(18):4753-4764, Sep. 15, 2012

Sausville and Burger, "Contributions of human tumor xenografts to anticancer drug development," *Cancer Res*, 66(7): 3351-3354, Apr. 2006.

Shakhova et al., "Sox10 promotes the formation and maintenance of giant congenital naevi and melanoma," *Nat. Cell Biol.*, 14(8):882-890, Aug. 2012.

Shibata et al., "Downstream region of the human tyrosinase-related protein gene enhances its promoter activity," Biochem. Biophys. Res. Commun., 184(2):568-575, Apr. 1992.

Srivastava, "Immunotherapy of human cancer: lessons from mice," *Nat Immunol.*, 1(5):363-366, Nov. 2000.

Suzuki et al., "Structural organization of the human mitochondrial cytochrome c1 gene," J. Biol. Chem., 264(3):1368-1374, Jan. 1989.

Thomas and Massagúe, "TGF-beta directly targets cytotoxic T cell functions during tumor evasion of immune surveillance.," Cancer Cell, 8(5):369-380, Nov. 2005.

Van Belle et al., "Melanoma-associated expression of transforming growth factor-beta isoforms," *Am J Pathol.*, 148(6):1887-1894, Jun. 1996.

Wagner et al., "Targeted nucleic acid delivery into tumors: new avenues for cancer therapy," *Biomed Pharmacother.*, 58(3):152-161, Apr. 2004.

Willmon et al., "Vesicular stomatitis virus-induced immune suppressor cells generate antagonism between intratumoral oncolytic virus and cyclophosphamide," Mol. Ther., 19(1):140-149, Jan. 2010.

(56) References Cited

OTHER PUBLICATIONS

Wongthida et al., "VSV oncolytic virotherapy in the B16 model depends upon intact MyD88 signaling," Mol. Ther., 19(1):150-158, Jan. 2011.
Yoshida et al., "Development of gene therapy to target pancreatic cancer," *Cancer Sci.*, 95(4): 283-289, Apr. 2002
Zhuang et al., "C-MYC overexpression is required for continuous suppression of oncogene-induced senescence in melanoma cells," *Oncogene*, 27(52):6623-6634, Nov. 6, 2008.
GenBank® Accession No. AAB29640, GI: 544859, "N-ras [*Homo sapiens*]," Sep. 23, 1994, 1 page.
GenBank® Accession No. AC_000025.1, GI: 83280973, "Mus musculus strain mixed chromosome 3, alternate assembly Mm_Celera, whole genome shotgun sequence," Oct. 19, 2010, 2 pages.
GenBank® Accession No. AF047043.1, "Mus musculus Sox-10 protein (Sox10) mRNA, complete cds," Jun. 27, 1998, 2 pages.
GenBank® Accession No. AF063658 GI: 3132832, "*Homo sapiens* vascular endothelial growth factor receptor 2 (KDR) mRNA, complete cds," May 16, 1998, 2 pages.
GenBank® Accession No. AF399931.1 GI: 33307711, "*Homo sapiens* P-glycoprotein (ABCB1) mRNA, complete cds," Jun. 10, 2004, 2 pages.
GenBank® Accession No. AF493896.1 GI: 20147684, "*Homo sapiens* guanine nucleotide binding protein alpha q (GNAQ) mRNA, complete cds," Apr. 14, 2002, 1 pages.
GenBank® Accession No. AF493919.1 GI: 20147730, "*Homo sapiens* Ras family small GTP binding protein N-Ras (NRAS) mRNA, complete cds," Apr. 14, 2002, 1 page.
GenBank® Accession No. AY101192.1 GI: 21429238, "*Homo sapiens* CD44 antigen (CD44) mRNA, complete cds," Jun. 15, 2002, 2 pages.
GenBank® Accession No. AY101193.1 GI: 21429240, "*Homo sapiens* CD44 antigen (CD44) mRNA, complete cds," Jun. 15, 2002, 2 pages.
GenBank® Accession No. AY234788.1 GI: 34539754, "*Homo sapiens* P-glycoprotein ABCB5 mRNA, complete cds," Nov. 17, 2003, 2 pages.
GenBank® Accession No. AY425006.1 GI: 40795902, "*Homo sapiens* P-glycoprotein 1 (ABCB1) mRNA, partial cds, alternatively spliced," Apr. 27, 2004, 1 page.
GenBank® Accession No. AY864315.1 GI: 57791235, "Mus musculus strain BALB/c multidrug resistance protein 1a (Abcb1 a) mRNA, complete cds," Jan. 19, 2005, 2 pages.
GenBank® Accession No. BC057583.1 GI: 34785834, "Mus musculus guanine nucleotide binding protein, alpha q polypeptide, mRNA (cDNA clone MGC:67083 Image:6408959), complete cds," Aug. 11, 2006, 3 pages.
GenBank® Accession No. BC061634.1 GI: 38197294, "Mus musculus Y box protein 1, mRNA (cDNA clone MGC:68144 Image:6530605), complete cds," Sep. 1, 2006, 3 pages.
GenBank® Accession No. BC071708.1 GI: 47940505, "*Homo sapiens* Y box binding protein 1, mRNA (cDNA clone MGC:87995 Image:4361396), complete cds," Jun. 23, 2006, 3 pages.
GenBank® Accession No. BC076598.1 GI: 49903295, "Mus musculus tyrosinase-related protein 1, mRNA (cDNA clone MGC:96635 Image:30613975), complete cds," Jul. 15, 2006, 3 pages.
GenBank® Accession No. BT020029 GI: 54696919, "*Homo sapiens* SRY (sex determining region Y)-box 10 mRNA, complete cds," Oct. 28, 2004, 2 pages.
GenBank® Accession No. CAG28611, GI: 47115303, "TYRP1 [*Homo sapiens*]," Oct. 16, 2008, 2 pages.
GenBank® Accession No. CR407683.1 GI: 47115302, "*Homo sapiens* full open reading frame cDNA clone RZPDo834D033D for gene TYRP1, tyrosinase-related protein 1 complete cds, without stopcodon," Oct. 16, 2008, 2 pages.
GenBank® Accession No. EU854148.1 GI: 194740429, "*Homo sapiens* multidrug resistance protein 1 mRNA, complete cds, alternatively spliced," Aug. 5, 2008, 2 pages.
GenBank® Accession No. EU884114.1 GI: 215400615, "Mus musculus strain C57BL/6 soluble vascular endothelial growth factor receptor 2 mRNA, complete cds," Nov. 15, 2010, 2 pages.
GenBank® Accession No. J04444, GI: 181239, "Human cytochrome c-1 gene, complete cds," Nov. 2, 1994, 3 pages.
GenBank® Accession No. J05114 GI: 37092, "Human mRNA for transforming growth factor-beta (TGF-beta)," Mar. 27, 1995, 2 pages.
GenBank® Accession No. JQ655148.1 GI: 406817019, "Mus musculus P-glycoprotein (Abcb5) mRNA, complete cds," Feb. 9, 2014, 2 pages.
GenBank® Accession No. M13177.1 GI: 201952, "Mouse transforming growth factor beta mRNA (TGF-beta), complete cds," Apr. 27, 1993, 2 pages.
GenBank® Accession No. M23234.1 GI: 187501, "Human membrane glycoprotein P (mdr3) mRNA, complete cds," Jun. 11, 1993, 2 pages.
GenBank® Accession No. M24417.1 GI: 2000329, "Mouse phosphoglycoprotein mdr1a mRNA, 3' end," Nov. 18, 1993, 2 pages.
GenBank® Accession No. M33581.1 GI: 199104, "Mouse P-glycoprotein (mdr1a) mRNA, complete cds," Apr. 27, 1993, 3 pages.
GenBank® Accession No. M62867 GI: 199820, "Mouse Y box transcription factor (MSY-1) mRNA, complete cds," Mar. 7, 1995, 2 pages.
GenBank® Accession No. NC_000069.6 GI: 372099107, "Mus musculus strain C57BL/6J chromosome 3, MGSCv37 C57BL/6J," Oct. 19, 2010, 1 page.
GenBank® Accession No. NM_009863 GI: 409168309, "Mus musculus cell division cycle 7 (S. cerevisiae) (Cdc7), transcript variant 2, mRNA," Oct. 18, 2012, 4 pages.
GenBank® Accession No. NM_000550, GI: 169881242, "*Homo sapiens* tyrosinase-related protein 1 (TYRP1), mRNA," Mar. 12, 2011, 4 pages.
GenBank® Accession No. NM_001067.3 GI: 300193028, "*Homo sapiens* topoisomerase (DNA) II alpha 170kDa (TOP2A), mRNA," Mar. 11, 2011, 9 pages.
GenBank® Accession No. NM_001134419.1 GI: 197313664, "*Homo sapiens* cell division cycle 7 (CDC7), transcript variant 2, mRNA," Mar. 10, 2011, 5 pages.
GenBank® Accession No. NM_001134420.1 GI: 197313666, "*Homo sapiens* cell division cycle 7 homolog (S. cerevisiae) (CDC7), transcript variant 3, mRNA," Mar. 11, 2011, 5 pages.
GenBank® Accession No. NM_001163941.1 GI: 255708476, "*Homo sapiens* ATP-binding cassette, sub-family B (MDR/TAP), member 5 (ABCB5), transcript variant 1, mRNA," Mar. 11, 2011, 6 pages.
GenBank® Accession No. NM_001163942.1 GI: 255708370, "*Homo sapiens* ATP-binding cassette, sub-family B (MDR/TAP), member 5 (ABCB5), transcript variant 3, mRNA," Mar. 11, 2011, 4 pages.
GenBank® Accession No. NM_001163993.2 GI: 574957217, "*Homo sapiens* ATP-binding cassette, sub-family B (MDR/TAP), member 5 (ABCB5), transcript variant 4, mRNA," Mar. 12, 2011, 4 pages.
GenBank® Accession No. NM_001177352.1 GI: 293629263, "Mus musculus myelocytomatosis oncogene (Myc), transcript variant 1, mRNA," Mar. 11, 2011, 5 pages.
GenBank® Accession No. NM_001177353.1 GI: 293629266, "Mus musculus myelocytomatosis oncogene (Myc), transcript variant 2, mRNA," Mar. 13, 2011, 5 pages.
GenBank® Accession No. NM_001177354.1 GI: 293629269, "Mus musculus myelocytomatosis oncogene (Myc), transcript variant 2, mRNA," Mar. 11, 2011, 5 pages.
GenBank® Accession No. NM_001177787 GI: 295293147, "Mus musculus CD44 antigen (Cd44), transcript variant 6, mRNA," Mar. 12, 2011, 5 pages.
GenBank® Accession No. NM_001282014.1 GI: 530537243, "Mus musculus tyrosinase-related protein 1 (Tyrp1), transcript variant 2, mRNA," Aug. 14, 2013, 4 pages.

(56) References Cited

OTHER PUBLICATIONS

GenBank® Accession No. NM_001282015.1 GI: 530537245, "Mus musculus tyrosinase-related protein 1 (Tyrp1), transcript variant 3, mRNA," Aug. 14, 2013, 4 pages.
GenBank® Accession No. NM_001430 GI: 262527236, "*Homo sapiens* endothelial PAS domain protein 1 (EPAS1), mRNA," Mar. 13, 2011, 6 pages.
GenBank® Accession No. NM_002154, GI: 38327038, "*Homo sapiens* heat shock 70kDa protein 4 (HSPA4), mRNA," Feb. 15, 2009, 5 pages.
GenBank® Accession No. NM_002524, GI: 185134767, "*Homo sapiens* neuroblastoma RAS viral (v-ras) oncogene homolog (NRAS), mRNA," Mar. 13, 2011, 5 pages.
GenBank® Accession No. NM_002524.4 GI: 334688826, "*Homo sapiens* neuroblastoma RAS viral (v-ras) oncogene homolog (NRAS), mRNA," Mar. 13, 2011, 5 pages.
GenBank® Accession No. NM_003503.3 GI: 197313663, "*Homo sapiens* cell division cycle 7 homolog (S. cerevisiae) (CDC7), transcript variant 1, mRNA," Mar. 13, 2011, 5 pages.
GenBank® Accession No. NM_004333.4 GI: 187608632, "*Homo sapiens* v-raf murine sarcoma viral oncogene homolog B1 (BRAF), mRNA," Mar. 13, 2011, 7 pages.
GenBank® Accession No. NM_004559.3 GI: 109134359, "*Homo sapiens* Y box binding protein 1 (YBX1), mRNA," Mar. 13, 2011, 5 pages.
GenBank® Accession No. NM_008139.5 GI: 145966786, "Mus musculus guanine nucleotide binding protein, alpha q polypeptide (Gnaq), mRNA," Mar. 12, 2011, 5 pages.
GenBank® Accession No. NM_009863 GI: 409168309, "Mus musculus cell division cycle 7 (S. cerevisiae) (Cdc7), mRNA," Mar. 10, 2012, 4 pages.
GenBank® Accession No. NM_010849.4 GI: 100913213, "Mus musculus myelocytomatosis oncogene (Myc), transcript variant 1, mRNA," Mar. 11, 2011, 5 pages.
GenBank® Accession No. NM_010937.2 GI: 372099107, "Mus musculus neuroblastoma ras oncogene (Nras), mRNA," Mar. 13, 2011, 4 pages.
GenBank® Accession No. NM_011075 GI: 161169006, "Mus musculus ATP-binding cassette, sub-family B (MDR/TAP), member 1B (Abcb1b), mRNA," Mar. 10, 2011, 7 pages.
GenBank® Accession No. NM_011623, "Mus musculus topoisomerase (DNA) II alpha (Top2a), mRNA," Mar. 11, 2012, 7 pages.
GenBank® Accession No. NM_011732.2 GI: 113205058, "Mus musculus Y box protein 1 (Ybx1), mRNA," Mar. 13, 2011, 5 pages.
GenBank® Accession No. NM_029961 XM_906632 GI: 255708374, "Mus musculus ATP-binding cassette, sub-family B (MDR/TAP), member 5 (Abcb5), mRNA," Mar. 11, 2011, 4 pages.
GenBank® Accession No. NM_031202.3 GI: 530537240, "Mus musculus tyrosinase-related protein 1 (Tyrp1), mRNA," Mar. 11, 2011, 4 pages.
GenBank® Accession No. NM_139294.5 GI: 153791903, "Mus musculus Braf transforming gene (Braf), mRNA," Feb. 27, 2011, 7 pages.
GenBank® Accession No. NM_178559.5 GI: 255708475, "*Homo sapiens* ATP-binding cassette, sub-family B (MDR/TAP), member 5 (ABCB5), transcript variant 2, mRNA," Mar. 13, 2011, 6 pages.
Genbank® Accession No. NM002524, "*Homo sapiens* neuroblastoma RAS viral (v-ras) oncogene homolog (NRAS), mRNA," Mar. 13, 2011.
GenBank® Accession No. NP_002145, GI: 38327039, "heat shock 70kDa protein 4 [*Homo sapiens*]," Feb. 15, 2009, 2 pages.
GenBank® Accession No. NP_061820, GI: 11128019, "cytochrome c [*Homo sapiens*]," Mar. 11, 2011, 2 pages.
GenBank® Accession No. NW_004078038.1, "*Homo sapiens* chromosome 9 genomic scaffold, alternate assembly CHM1_1.0, whole genome shotgun sequence," Nov. 2, 2012, 4 pages.
GenBank® Accession No. U40038.1 GI: 1181670, "Human GTP-binding protein alpha q subunit (GNAQ) mRNA, complete cds," Feb. 7, 1996, 2 pages.
GenBank® Accession No. V00568 GI: 34815, "Human mRNA encoding the c-myc oncogene," Oct. 7, 2008, 2 pages.
GenBank® Accession No. X02812 GI: 37092, "Human mRNA for transforming growth factor-beta (TGF-beta)," Mar. 27, 1995, 2 pages.
GenBank® Accession No. X51420.1 GI: 37512, "*Homo sapiens* mRNA for tyrosinase-related protein precursor (TYRP1)," Oct. 7, 2008, 2 pages.
GenBank® Accession No. X57621.1 GI: 55450, "M.musculus YB-1 mRNA," Apr. 18, 2005, 2 pages.
GenBank® Accession No. X58723 GI: 34522, "Human MDR1 (multidrug resistance) gene for P-glycoprotein," Nov. 14, 2006, 2 pages.
GenBank® Accession No. X59732 GI: 34522, "Human MDR1 (multidrug resistance) gene for P-glycoprotein," Nov. 14, 2006, 2 pages.
GenBank® Accession No. XM_001002680 GI: 255708374, "Predicted: Mus musculus ATP-binding cassette, sub-family B (MDR/TAP), member 5 (Abcb5), mRNA," Jun. 20, 2007, 2 pages.
GenBank® Accession No. XM_005250045.1 GI: 530387105, "Predicted: *Homo sapiens* v-raf murine sarcoma viral oncogene homolog B (BRAF), transcript variant X1, mRNA," Aug. 13, 2013, 4 pages.
GenBank® Accession No. XM_005250046.1 GI: 530387107, "Predicted: *Homo sapiens* v-raf murine sarcoma viral oncogene homolog B (BRAF), transcript variant X2, mRNA," Aug. 13, 2013, 4 pages.
GenBank® Accession No. XM_005250047.1 GI: 530387109, "Predicted: *Homo sapiens* v-raf murine sarcoma viral oncogene homolog B (BRAF), transcript variant X3, mRNA," 2 pages, Apr. 2013.
GenBank® Accession No. XM_005251574.1 GI: 530390132, "Predicted: *Homo sapiens* tyrosinase-related protein 1 (TYRP1), transcript variant X1, mRNA," Feb. 3, 2014, 3 pages.
GenBank® Accession No. XM_005270904.1 GI: 530362706, "Predicted: *Homo sapiens* Y box binding protein 1 (YBX1), transcript variant X1, mRNA," Aug. 13, 2013, 2 pages.
European Search Report for Application No. 11742816.9 dated Jul. 10, 2013, 8 pages.
International Preliminary Report on Patentability for PCT/US2013/031953 mailed Sep. 25, 2014, 5 pages.
International Preliminary Report on Patentability in Application No. PCT/US2011/024397, mailed Aug. 23, 2012, 6 pages.
International Search Report and Written Opinion for Application No. PCT/US2013/031953, mailed Jul. 4, 2013, 8 pages.
International Search Report and Written Opinion in Application No. PCT/US2011/024397, mailed Oct. 25, 2011, 10 pages.
International Search Report and Written Opinion in Application No. PCT/US2015/021574, mailed Jul. 8, 2015, 23 pages.
International Search Report and Written Opinion in Application No. PCT/US2015/021576, mailed Jul. 10, 2015, 13 pages.

\* cited by examiner

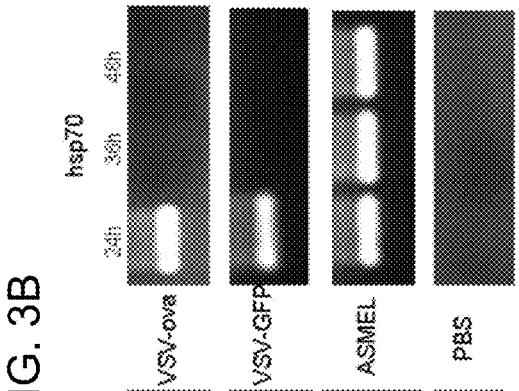
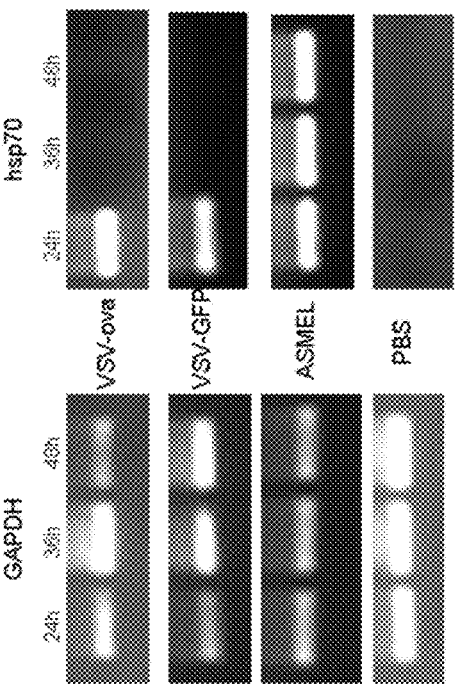
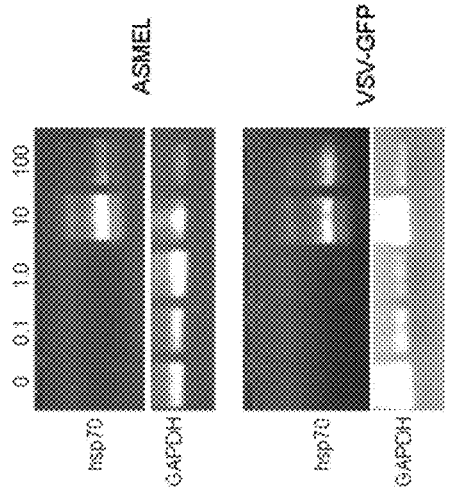
FIG. 3A
FIG. 3B

| Splenocyte/LN cultures infected by VSV | | IL-17 secretion (stimulator B16ova lysate) | |
|---|---|---|---|
| MOI of infection | Hsp70 induction | No added hsp70 | Added rhsp70 |
| ASMEL 0.1 | - | - | + |
| 1.0 | - | - | + |
| 10 | + | + | ++ |
| 100 | + | +++ | ++ |
| VSV-GFP 0.1 | - | - | - |
| 1.0 | - | - | - |
| 10 | + | - | - |
| 100 | + | - | - |

| Splenocytes/lymph node cells infected with ASMEL (MOI 10) | Hsp70 induction | IL-17 | |
|---|---|---|---|
| | | -rhsp70 | +rhsp70 |
| C57BL/6 | +++ | +++ | |
| MyD88-/- | + | - | + |
| TLR4-/- | - | - | ++ |
| TLR7-/- | +++ | - | - |

FIG. 3E

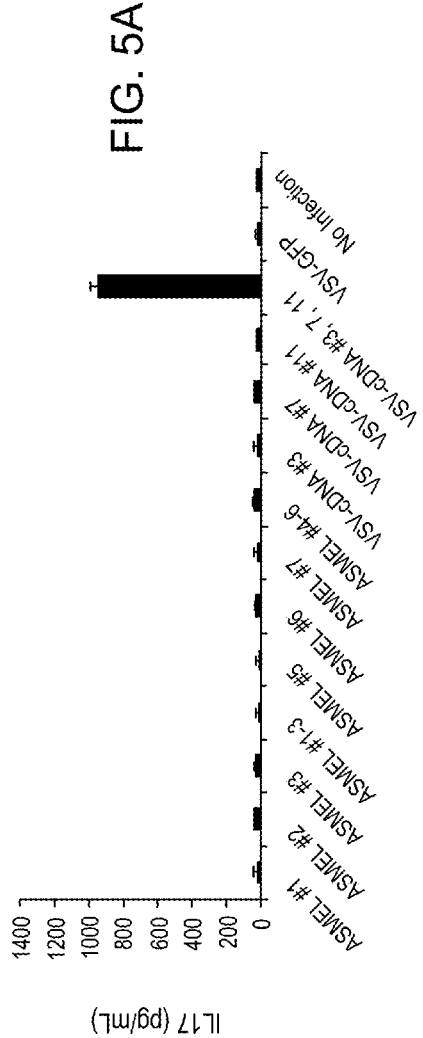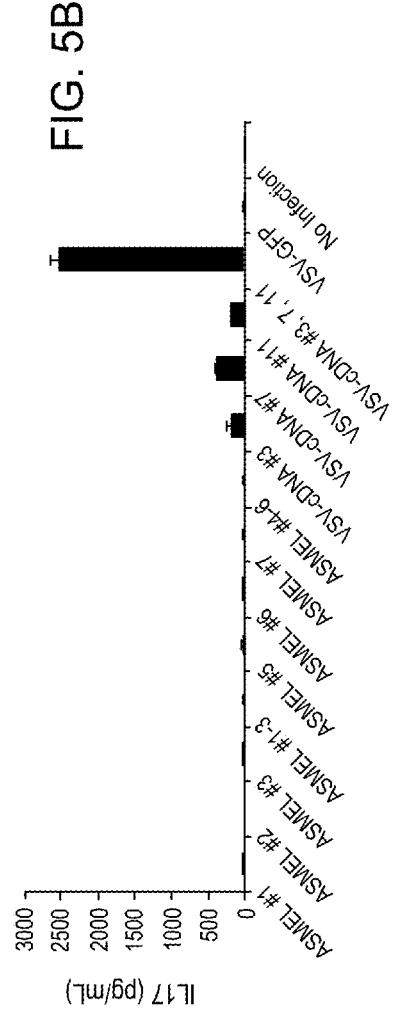

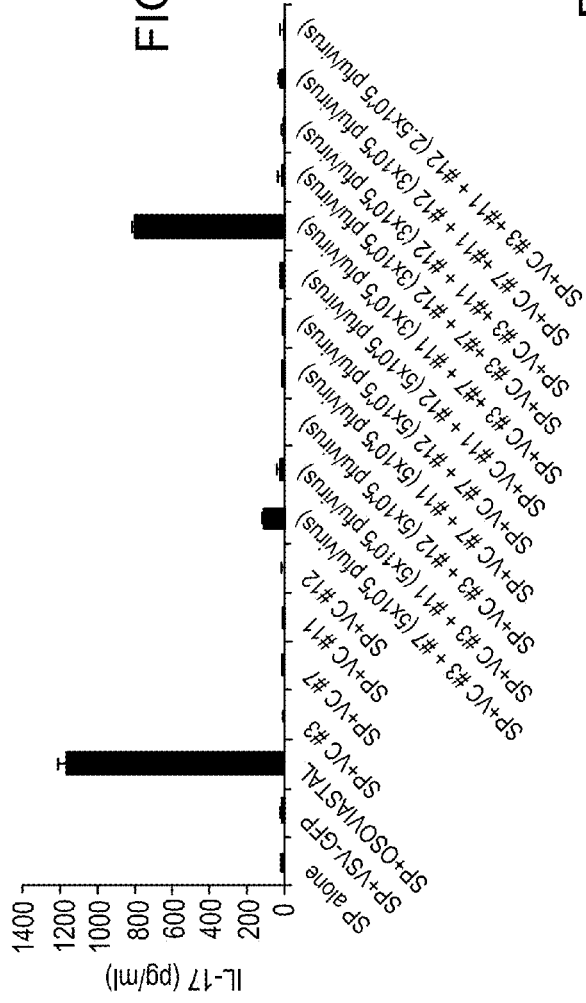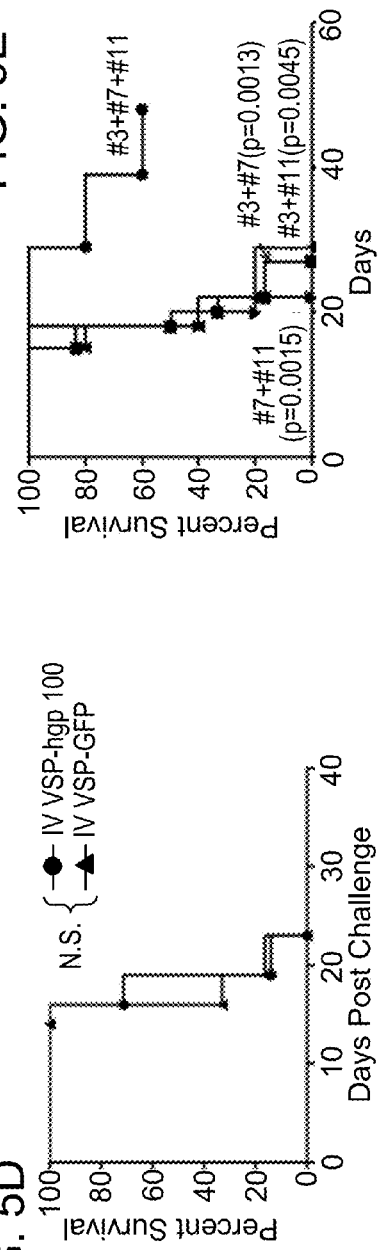
FIG. 5C
FIG. 5D
FIG. 5E

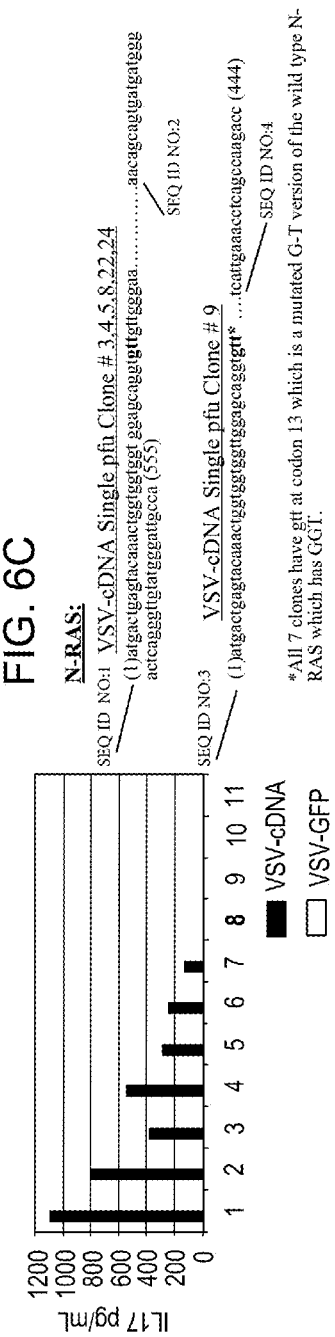

METHODS AND MATERIALS FOR TREATING CANCER

CROSS-REFERENCE TO RELATED APPLICATIONS

This application is a National Stage application under 35 U.S.C. 371 of International Application No. PCT/US2013/031953, having an International Filing Date of Mar. 15, 2013 which claims the benefit of U.S. Provisional Application Ser. No. 61/611,387, filed Mar. 15, 2012. The disclosure of the prior application is considered part of (and is incorporated by reference in) the disclosure of this application.

STATEMENT AS TO FEDERALLY SPONSORED RESEARCH

This invention was made with government support under grant numbers CA107082, CA130878, and CA132734 awarded by the National Institutes of Health. The government has certain rights in the invention.

BACKGROUND

1. Technical Field

This document relates to methods and materials for treating cancer. For example, this document relates to methods and materials for identifying antigens and combinations of antigens that can be used to treat cancer. This document also relates to methods and materials for using combinations of antigens to treat cancer (e.g., melanoma).

2. Background Information

Cancer is a serious illness that affects many people every year. In general, there are several common methods for treating cancer: surgery, chemotherapy, radiation therapy, immunotherapy, and biologic therapy. When initially diagnosed with cancer, a cancer specialist such as an oncologist can provide a patient with various cancer treatment options. Typically, an oncologist will recommend the best treatment plan based on the type of cancer, how far it has spread, and other important factors like the age and general health of the patient.

SUMMARY

This document provides methods and materials for treating cancer. For example, this document provides methods and materials for identifying antigens and combinations of antigens that can be used to treat cancer. This document also provides combinations of antigens having the ability to reduce established tumors within a mammal (e.g., a human). As described herein, screening techniques can be used to identify antigens and combinations of antigens that can be used to treat cancer. For example, nucleic acids encoding antigens having the ability, either alone or in combination with one or more other antigens, to stimulate an anti-cancer response can be identified from a nucleic acid library (e.g., a VSV-expressed cDNA library) using a screening technique that includes contacting immune cells with an aliquot of the nucleic acid library to form a collection of virally infected cells, obtaining a cell from the collection of virally infected cells that has the ability to secrete a cytokine polypeptide (e.g., a IL-17 polypeptide), and determining the sequence of the nucleic acid member (e.g., VSV-expressed cDNA) of that obtained cell. In some cases, the immune cells can be cells that were obtained from a mammal that exhibited a reduction in the number of cancer cells following administration of a nucleic acid library (e.g., the same nucleic acid library used to identify antigens). In some cases, multiple rounds of screening can be performed as set forth, for example, in FIG. 6A.

As also described herein, combinations of antigens (e.g., a combination of an N-RAS antigen, a TYRP1 antigen, and a CYT-C antigen) can be used to treat cancer (e.g., melanoma). For example, VSV vectors designed to express an N-RAS antigen, a TYRP1 antigen, and a CYT-C antigen can be used to treat established tumors.

In general, one aspect of this document features a method for identifying, from a nucleic acid library, a nucleic acid encoding an antigen having the ability, either alone or in combination with one or more other antigens, to stimulate an anti-cancer response, wherein the nucleic acid library is a library of virally-expressed nucleic acid members and has the ability to stimulate an anti-cancer response when administered to a mammal having cancer. The method comprises, or consists essentially of, (a) contacting immune cells with an aliquot of the nucleic acid library to form a collection of virally infected cells, wherein the immune cells were obtained from a mammal that exhibited a reduction in the number of cancer cells following administration of a first nucleic acid library, (b) obtaining a cell from the collection of virally infected cells that has the ability to secrete a cytokine polypeptide, wherein the cell contains a nucleic acid member of the nucleic acid library, and (c) determining the sequence of the nucleic acid member of the cell, wherein the nucleic acid member is the nucleic acid encoding an antigen having the ability, either alone or in combination with one or more other antigens, to stimulate an anti-cancer response. The nucleic acid library can be a cDNA library. The nucleic acid library can be a VSV-expressed cDNA library. The immune cells can be immune cells that were obtained from a mammal that exhibited a reduction in the number of cancer cells following administration of a first nucleic acid library. The first nucleic acid library can be a cDNA library. The first nucleic acid library can be a VSV-expressed cDNA library or an expressed cDNA library via another virus, animal cell, bacterial cell, or fungus. The nucleic acid library and the first nucleic acid library can be the same library. The immune cells can be lymph node cells and splenocytes. The contacting step (a) can comprise contacting the immune cells with the aliquot in the presence of an hsp70 polypeptide. The hsp70 polypeptide can be a human hsp70 polypeptide. The aliquot can comprise a multiplicity of infection (MOI) of less than 10. The mammal can be a rodent or primate. The mammal can be a mouse. The mammal can be a human. The cytokine polypeptide can be an IL-17 polypeptide or a TNF-alpha polypeptide.

In another aspect, this document features a composition comprising, or consisting essentially of, nucleic acid encoding N-RAS, TYRP1, and CYT-C, wherein the composition comprises less than 100 separate nucleic acid molecules. The composition can comprise a nucleic acid molecule encoding the N-RAS, a nucleic acid molecule encoding the TYRP1, and a nucleic acid molecule encoding the CYT-C. The composition can comprise less than 50 separate nucleic acid molecules. The composition can comprise less than 10 separate nucleic acid molecules.

In another aspect, this document features a method of treating an established tumor within a mammal. The method comprises, or consists essentially of, administering to the mammal a composition comprising nucleic acid encoding an N-RAS antigen, a TYRP1 antigen, and a CYT-C antigen, wherein the composition comprises less than 100 separate nucleic acid molecules. The tumor can be a melanoma. The N-RAS antigen, the TYRP1 antigen, and the CYT-C antigen can be VSV-expressed.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

FIG. 5. Tumor specific immunity induced by VSV-cDNA libraries is mediated by combinations of antigens. A. LN/splenocyte cultures from ASMEL-vaccinated mice were screened for IL-17 secretion following no infection (lane 13); or with infection with $10^7$ pfu of individual single viruses from the parental, unselected ASMEL stock (AS-MEL #1-#6) (lanes 1-3, 5-7); with the selected viruses VSV-cDNA clone #3 (N-RAS), VSV-cDNA clone #7 (TYRP1), and VSV-cDNA clone #11 (CYT-C) (lanes 9-11), or with VSV-GFP (lane 13). In addition, infections were performed with three way combinations ($3 \times 10^6$ pfu of each virus) of ASMEL #1+#2+#3 (Lane 4); ASMEL #4+#5+#6 (Lane 8); or VSV-cDNA clones #3+#7+#11 (lane 12). B. The experiment of A above was repeated in the presence of TGF-β RII Fc Chimera to inhibit TGF-β in the cultures. C. Pooled LN/splenocyte cultures ($10^5$/well) from naive C57BL/6 mice were infected every two days with ASMEL or VSV-GFP over a two week period, with regular replenishment of the lymphoid cells. LN/splenocyte cultures were either left uninfected (lane 1); or infected with single viruses ($10^6$ pfu) VSV-GFP (lane 2); ASMEL parental virus stock (3); VSV-cDNA clone #3 (N-RAS) (4), VSV-cDNA clone #7 (TYRP1) (5), VSV-cDNA clone #11 (CYT-C) (6); VSV-cDNA clone #12 (TRIM33) (7). In addition, LN/splenocyte cultures were infected with two way combinations of viruses: clone #3 (N-RAS)+clone #7 (TYRP1) (8); clone #3 (N-RAS)+clone #11 (CYT-C) (9); clone #3 (N-RAS)+clone #12 (TRIM33) (10); clone #7+clone#11 (11); clone #7+clone#12 (12); clone #11+clone#12 (13). LN/splenocyte cultures were also infected with three way combinations of viruses: clone#3+clone#7+clone#11 (14); clone#3+clone#7+clone#12 (15); clone#3+clone#11+clone#12 (16); clone#7+clone#11+clone#12 (17). Finally, cultures were also infected with a four way combination of clone#3+clone#7+clone#11+clone#12 (18). 48 hours following the final infection with virus, cultures were stimulated with B16 melanoma cell lysates for three consecutive days. 48 hours later supernatants were assayed for IL-17 by ELISA. D. Mice bearing 5 day established B16 tumors were treated (n=6-8/group) with intravenous injections of VSV-GFP or VSV-expressing the melanoma associated antigen hgp100. E. Mice bearing 5 day established B16 tumors were treated (n=6-8/group) with 9 intravenous injections on days 6, 7, 8, 13, 14, 15, 20, 21, and 22 of two way combinations (total viral dose $10^7$ pfu/injection; $5 \times 10^6$ pfu of each individual virus) of either VSV-cDNA clone #3 (N-RAS)+clone#7 (TYRP1); clone#3 (N-RAS)+clone #11 (CYT-C); or clone #7+clone#11. A fourth group was treated with a three way combination (total viral dose $10^7$ pfu/injection; $3 \times 10^6$ pfu of each individual virus) of VSV-cDNA clone#3 (N-RAS)+clone#7 (TYRP1)+clone#11 (CYT-C). Survival with time is shown.

FIG. 6. Cloning VSV-cDNA viruses from the ASMEL. FIG. 6B. IL-17 secreted from infection of LN/splenocyte cultures of ASMEL vaccinated mice in the presence of recombinant hsp70 with neat (1) or 1:10 dilution (2) of ASMEL or VSV-GFP; or with $10^4$ (3), $10^2$ (4), 10 (5), 1 (6), 0 (7), $10^{-1}$ (8), $10^{-2}$ (9) $10^{-3}$ (10) or $10^{-4}$ (11) pfu of the second round selected virus stock or VSV-GFP. FIG. 6C. Viruses harvested after 48-72 hours from 24 of these 'single pfu'-containing wells were screened by PCR, and their encoded cDNA inserts were sequenced. Representative sequences at the ends of these cDNA inserts are shown for the seven viruses encoding part of the human N-RAS oncogene (Genbank® Accession #NM002524), the four viruses encoding part of the human TYRP1 gene (Genbank® Accession #NM000550), and the two viruses encoding sequence of the human cytochrome C1 gene (Genbank® Accession #J04444).

DETAILED DESCRIPTION

This document provides methods and materials for treating cancer. For example, this document provides methods and materials for identifying antigens and combinations of antigens that can be used to treat cancer. This document also provides combinations of antigens having the ability to reduce established tumors within a mammal (e.g., a human).

Figure 6A:
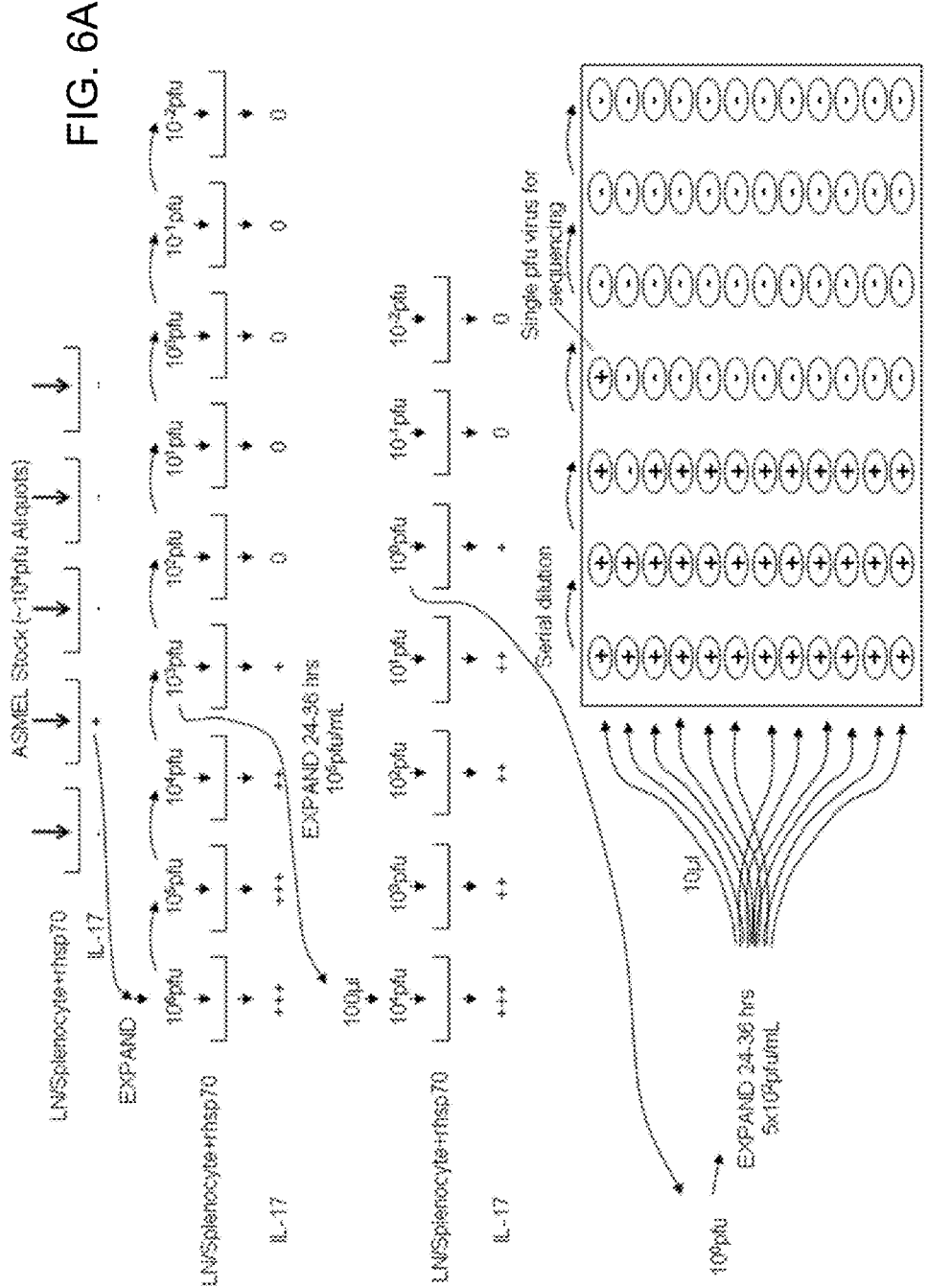
FIG. 6A contains an experimental scheme for cloning viruses. LN/splenocyte cultures ($10^4$/well) from ASMEL-vaccinated mice were screened for secretion of IL-17 induced by infection with aliquots of ~$10^4$ pfu of the parental ASMEL virus stock in the presence of recombinant hsp70. Aliquots that contained virus competent for inducing the IL-17 recall response were pooled and expanded in BHK cells (24-36 hours). New LN/splenocyte cultures from ASMEL-vaccinated mice were infected with serial dilutions of this expanded stock in the presence of recombinant hsp70, and assayed for IL-17 production. The highest dilution of the virus stock (~$10^3$ pfu) that induced IL-17 at levels significantly above background (>100 pg/mL) was amplified by passaging through BHK cells for 24-36 hours. Serial dilutions of this expanded stock were screened for their ability to induce IL-17 (see FIG. 6B). 10 μL aliquots of the highest dilution of the virus which induced IL-17 ('0 pfu') were used as the starting point for limiting dilution cloning on BHK cells to identify the dilution at which a single virus particle generated cytopathic effect (+).

In general, nucleic acids encoding antigens having the ability, either alone or in combination with one or more other antigens, to stimulate an anti-cancer response can be identified from a nucleic acid library using a screening technique that includes contacting immune cells with an aliquot of a nucleic acid library to form a collection of virally infected cells (see, e.g., FIG. 6A). In some cases, the library can be a VSV-expressed cDNA library. Other examples of libraries include, without limitation, those described in International Patent Application Publication No. WO2011/100468. The immune cells can be immune cells obtained from a mammal that exhibited a reduction in the number of cancer cells following administration of a nucleic acid library. This nucleic acid library can be the same library used to form the collection of virally infected cells or a different library from that used to form the collection of virally infected cells. Examples of immune cells that can be used include, without limitation, lymph node cells, splenocytes, peripheral circulating lymphocytes, bone marrow derived cells, or combinations thereof. In some cases, the immune cells can be exposed to the aliquot of the nucleic acid library in the presence of an hsp70 polypeptide (e.g., a human hsp70 polypeptide) or another activating immunogenic polypeptide.

Once the collection of virally infected cells is obtained, that collection of cells can be screened to identify those cells or those wells containing cells that have the ability to secrete a cytokine polypeptide. Any appropriate cytokine polypeptide can be used including, without limitation, an IL-17 polypeptide, an interferon polypeptide, a TNF-alpha polypeptide, an activating cytokine polypeptide, or a combination thereof. In some cases, multiple rounds of screening can be performed as set forth, for example, in FIG. 6A.

Once a cell or cells having the ability to secrete a cytokine polypeptide (e.g., an IL-17 polypeptide) are obtained, the nucleic acid library member (e.g., VSV-expressed cDNA) within that obtained cell can be determined Standard sequencing techniques can be used to determine the nucleic acid sequence of the library member present within the isolated cell. Such sequences can be used to identify the amino acid sequence of the antigen having the ability to induce an anti-cancer response either alone or when used in combination with other antigens.

As described herein, the screening methods and materials provided herein can be used to identify combinations of antigens having the ability to treat established tumors. For example, a combination of an N-RAS antigen, a TYRP1 antigen, and a CYT-C antigen can be used to treat cancer (e.g., melanoma). In some cases, one or more viral vectors (e.g., VSV vectors) designed to express an N-RAS antigen, a TYRP1 antigen, and a CYT-C antigen can be used to treat established tumors. An N-RAS antigen can have the amino acid sequence set forth in GenBank® Accession No. AAB29640 (GI No. 544859), or a fragment of such an amino acid sequence that is between about 7 and 400 amino acid residues (e.g., between about 10 and 400 amino acid residues, between about 15 and 400 amino acid residues, between about 20 and 400 amino acid residues, between about 25 and 400 amino acid residues, between about 30 and 400 amino acid residues, or between about 30 and 200 amino acid residues) in length. A TYRP1 antigen can have the amino acid sequence set forth in GenBank® Accession No. CAG28611 (GI No. 47115303), or a fragment of such an amino acid sequence that is between about 7 and 527 amino acid residues (e.g., between about 10 and 527 amino acid residues, between about 15 and 527 amino acid residues, between about 20 and 527 amino acid residues, between about 25 and 527 amino acid residues, between about 30 and 527 amino acid residues, or between about 30 and 200 amino acid residues) in length. A CYT-C antigen can have the amino acid sequence set forth in GenBank® Accession No. NP_061820 (GI No. 11128019), or a fragment of such an amino acid sequence that is between about 7 and 200 amino acid residues (e.g., between about 10 and 200 amino acid residues, between about 15 and 200 amino acid residues, between about 20 and 200 amino acid residues, between about 25 and 200 amino acid residues, between about 30 and 200 amino acid residues, or between about 30 and 150 amino acid residues) in length.

The invention will be further described in the following examples, which do not limit the scope of the invention described in the claims.

EXAMPLES

Example 1

Identifying Antigens that Act Co-Operatively to Treat Established Tumors

Materials and Methods
Cells and Viruses

B16 cells are cells derived from a murine melanoma syngeneic to C57BL/6 mice (H2-K$^b$) as described elsewhere (Linardakis et al., *Cancer Res.*, 62, 5495-5504 (2002)). TRAMP-C2 (TC2) cells are cells derived from a prostate tumor that arose in a TRAMP mouse and were characterized as described elsewhere (Kottke et al., *Cancer Res.*, 67:11970-11979 (2007); and Kottke et al., *Nat. Med.*, 17(7): 854-9 (2011)). VSV-cDNA libraries were generated as described elsewhere (Kottke et al., *Nature Med.*, 17:854-859 (2011)). Briefly, cDNA from two human melanoma cell lines, Mel624 and Mel888, was pooled, cloned into the pCMV.SPORT6 cloning vector (Invitrogen, CA), and amplified by PCR. The PCR amplified cDNA molecules were size fractionated to below 4 kb for ligation into the parental VSV genomic plasmid pVSV-XN2 (Fernandez et al., *J. Virol.*, 76:895-904 (2002)) between the G and L genes. The complexity of the cDNA library (termed an ASMEL cDNA library) cloned into the VSV backbone plasmid between the Xho1-Nhe1-sites was 7.0×10$^6$ colony forming units. This library was termed ASMEL as it expressed Altered Self Melanoma Epitopes (in a murine context) from the viral Library.

Virus was generated from BHK cells by co-transfection of pVSV-XN2-cDNA library DNA along with plasmids encoding viral genes as described elsewhere (Fernandez et al., *J. Virol.*, 76:895-904 (2002)). Virus was expanded by a single round of infection of BHK cells and purified by sucrose gradient centrifugation.

VSV-GFP was generated by cloning the cDNA for GFP into the plasmid pVSV-XN2 as described elsewhere (Fernandez et al., *J. Virol.*, 76:895-904 (2002)). Monoclonal VSV-GFP was obtained by plaque purification on BHK-21 cells. Concentration and purification were performed by sucrose gradient centrifugation. Titers were measured by standard plaque assays on BHK-21 cells as described elsewhere (Fernandez et al., *J. Virol.*, 76:895-904 (2002)).

Preparation of Pmel, OT-I, or C57BL/6 Normal Lymphocytes

OT-I mice and Pmel mice were bred (Overwijk et al., *J. Exp. Med.*, 198:569-580 (2003); and Hogquist et al., *Cell*, 76:17 (1994)). Pmel T cells express a transgenic T cell receptor specific for the KVPRNQDWL (SEQ ID NO:11) polypeptide from the human, melanocyte-specific gp100 antigen (hgp100$_{25-33}$), which is presented in the context of the murine H-2D$^b$ MHC Class I molecule by C57BL/6 mice (Overwijk et al., *J. Exp. Med.*, 198:569-580 (2003)). The OT-I mouse strain is on a C57BL/6 background (H-2K$^b$) and expresses a transgenic T-cell receptor Vα2 specific for the SIINFEKL (SEQ ID NO:12) polypeptide of ovalbumin in the context of MHC class I, H-2K$^b$ (Hogquist et al., *Cell*, 76:17 (1994)). Spleen and lymph nodes from Pmel, OT-I, or C57BL/6 mice were crushed through a 100 μm filter to prepare a single-cell suspension. RBCs were removed by a 2-minute incubation in ACK buffer. These pooled LN/splenocyte cultures were either used in the assays described or, where appropriate, CD8$^+$ T cells were isolated using the MACS CD8$^+$ (Ly-2) Microbead magnetic cell sorting system (Miltenyi Biotec). FACS analysis demonstrated cultures typically of >98% CD8$^+$ T cells, <2% CD4$^+$ T cells, <0.1% NK1.1+ve cells. Viable cells were purified by density gradient centrifugation using Lympholyte-M (Cedarlane Laboratories).

In Vivo Studies

C57BL/6 mice were purchased from Jackson Laboratories at 6-8 weeks of age. TLR4 and TLR7 KO mice (TLR4$^{-/-}$, TLR7$^{-/-}$) were purchased from The Jackson Laboratory (Bar Harbor, Me.) at 6-8 weeks of age. MyD88 KO mice (MyD88$^{-/-}$) were obtained from Dr. Pease (Mayo Clinic). To establish subcutaneous tumors, 2×10$^5$ B16 cells in 100 μL of PBS were injected into the flank of mice. Intravenous injections of virus were administered in 100 μL volumes. For survival studies, tumor diameter in two dimensions was measured three times weekly using calipers, and mice were killed when tumor size was approximately 1.0× 1.0 cm in two perpendicular directions. Immune cell depletions were performed by i.p. injections (0.1 mg per mouse) of anti-CD8 (Lyt 2.43), anti-CD4 (GK1.5), both from the Monoclonal Antibody Core Facility, Mayo Clinic; anti-NK (anti-asialo-GM-1, Cedarlane) and IgG control (ChromPure Rat IgG, Jackson ImmunoResearch) at day 4 after tumor implantation and then weekly thereafter. FACS analysis of spleens and lymph nodes confirmed subset specific depletions.

Reverse Transcriptase PCR

RNA was prepared from cell cultures with the QIAGEN RNA extraction kit. 1 µg total cellular RNA was reverse transcribed in a 20 µL volume using oligo-(dT) as a primer. A cDNA equivalent of 1 ng RNA was amplified by PCR with gene specific primers or GAPDH as a loading control.

ELISA Analysis for IL-17, TGF-β or IFN-γ Secretion

Typically, $10^6$ splenocytes were incubated at 37° C. with freeze thaw lysates from tumor cells in triplicate, every 24 hours for 3 days. 48 hours later, cell-free supernatants were collected and tested by specific ELISA for IL-17 (R&D Systems), TGF-β, or IFN-γ (BD OptEIA; BD Biosciences).

Dependence of suppression on TGF-β was assayed using recombinant human TGF-β sRII/Fc chimera (R&D Systems, Minneapolis, Minn.), a 159-amino acid extracellular domain of human TGF-β receptor type II fused to the Fc region of human IgG1 (Willmon et al., *Mol. Ther.*, 19:140-149 (2010); and Thomas and Massague, *Cancer Cell* 8:369-380 (2005)).

Statistics

Survival data from the animal studies was analyzed using the log rank test, and the two-sample unequal variance student's t test analysis was applied for in vitro assays. Statistical significance was determined at the level of p<0.05.

Results

Altered Self Melanoma Epitope VSV-cDNA Library cDNA from two human melanoma cell lines, Mel624 and Mel888, was cloned into VSV. This library was termed ASMEL and had titers of between $5 \times 10^6$ to $1 \times 10^7$ pfu/mL.

Figure 1A:
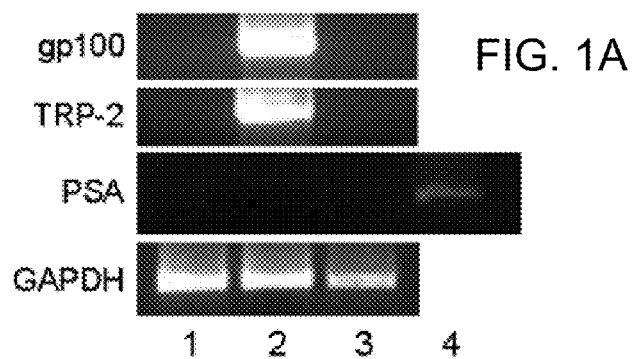
FIG. 1. Validation of the Altered Self Melanoma Epitope VSV-cDNA Library. A. BHK cells were screened for expression of the melanocyte/melanoma-specific genes gp100 and TRP-2, the prostate specific PSA gene, or GAPDH by rtPCR following infection with no virus (lane 1), the ASMEL (MOI~1) (lane 2), or VSV-GFP (lane 3). Lane 4, cDNA from the human LnCap prostate cancer cell line. B. $10^6$ C57BL/6 splenocytes infected 24 hours previously with either VSV-GFP, ASMEL, or a VSV-cDNA library derived from normal human prostate tissue (MOI~10) were co-cultured with either naïve Pmel or OT-I T cells (E:T ratio of 5:1) 4 and 28 hours following virus infection. 24-48 hours later, supernatants were assayed for IFN-γ, to detect transfer of expression of the hgp100$_{25-33}$ KVPRNQDWL (SEQ ID NO:11) polypeptide from the virus to infected splenocytes and subsequent presentation to the Pmel T cells. C. Lane 1, splenocytes alone (no virus, no T cells); Lane 2, splenocytes infected with VSV-GFP with added Pmel T cells; Lane 3, splenocytes infected with ASMEL with added OT-I T cells which recognize the irrelevant SIINFEKL (SEQ ID NO:12) epitope of the OVA antigen; Lane 4, splenocytes infected with ASMEL with added Pmel T cells, which recognize the hgp100$_{25-33}$ KVPRNQDWL (SEQ ID NO:11) epitope; Lane 5, splenocytes infected with VSV-cDNA from normal human prostate with added Pmel T cells; Lane 6, naive Pmel alone (no splenocytes, no virus).
Figure 1B:
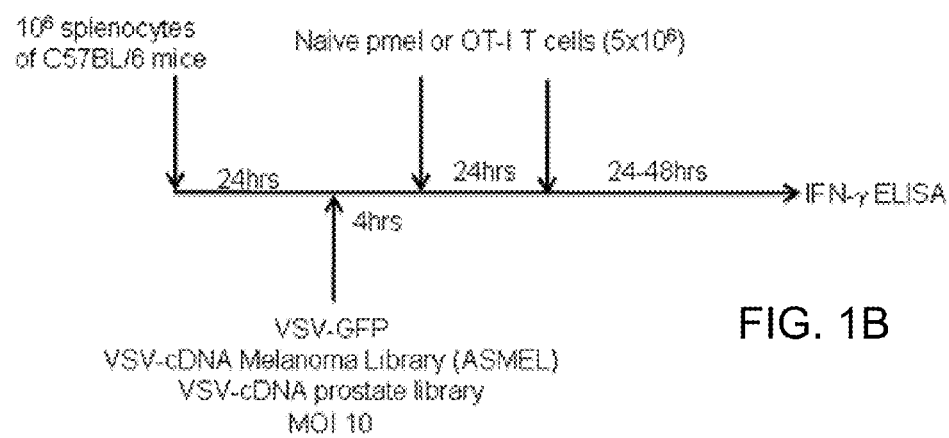
Figure 1C:
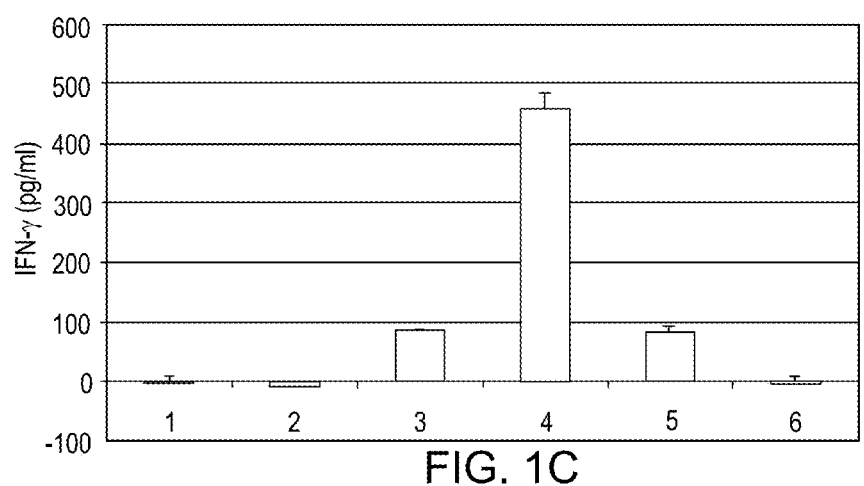

Cells infected with the ASMEL virus expressed the melanoma-specific genes gp100 and TRP-2, but not the prostate specific PSA gene (FIG. 1A). In addition, C57BL/6 splenocytes infected with the ASMEL induced IFN-γ from naive Pmel T cells (FIGS. 1B and 1C), indicating that the ASMEL transferred expression of the KVPRNQDWL (SEQ ID NO:11) polypeptide epitope from the human, melanocyte-specific gp100 antigen (hgp100$_{25-33}$), which is presented by both human HLA-A*0201 and mouse H-2K$^b$, to T cells (Overwijk et al., *J. Exp. Med.*, 198:569-580 (2003)). Splenocytes infected with no virus, VSV-GFP, or a VSV-cDNA library derived from normal human prostate cells (Kottke et al., *Nature Med.*, 17:854-859 (2011)), did not activate Pmel (FIG. 1C) other than through non-specific, VSV-mediated T cell activation, as described elsewhere (Galivo et al., *Human Gene Ther.*, 21:439-450 (2010); Galivo et al., *Gene Ther.*, 17:158-170 (2010); Wongthida et al., *Mol. Ther.*, 19:150-158 (2011); and Willmon et al., *Mol. Ther.*, 19:140-149 (2010)). In addition, splenocytes infected with the ASMEL did not activate OT-I T cells, which recognize the SIINFEKL (SEQ ID NO:12) epitope of the irrelevant ovalbumin antigen (Hogquist et al., *Cell*, 76:17 (1994); FIG. 1C). Therefore, the human melanoma cDNA library in VSV transferred expression of T cell activating epitopes to target cells.

Figure 2A:
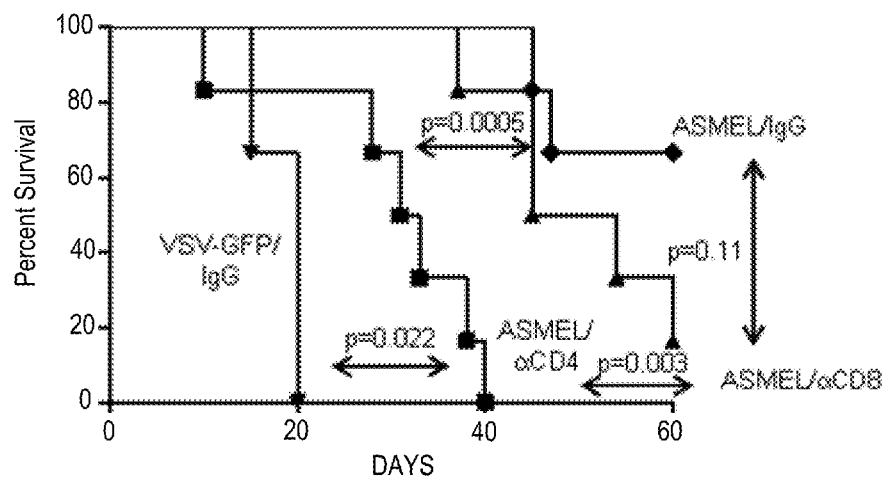
FIG. 2. Intravenous ASMEL Cures Established B16 Melanomas. A. Mice bearing 5 day established B16 tumors were either mock depleted (IgG), or were depleted of CD4+ or CD8+ T cells. Mice were then administered 9 intravenous injections of the ASMEL or VSV-GFP ($10^7$ pfu/injection) on days 8, 9, 10, 15, 16, 17, 22, 23, and 24. Survival with time is shown. B and C. 6 months after treatment with 9 intravenous injections of ASMEL the only overt symptoms of autoimmune vitiligo were a whitening of the whiskers (B) and tails (B and C) compared to age matched mice treated with PBS. D. Pooled LN and splenocytes ($10^6$/well) from mice treated with 9 intravenous injections of ASMEL were infected 24 hours later with ASMEL or VSV-GFP (MOI of about 10). 24 hours later, the cultures were replenished with an additional $10^6$ LN/splenocytes with a further round of virus infection 24 after that. 48 hours following the final infection with virus, cultures were stimulated with either prostate tumor TC2, or melanoma B16, cell lysates and 48 hours later supernatants were assayed for IL-17 by ELISA. Lanes 1-4, LN/splenocytes from ASMEL treated mice treated with VSV-GFP and no tumor lysate (1); VSV-GFP and B16 tumor lysate (2); ASMEL and B16 tumor lysate (3) or ASMEL and TC2 tumor lysate (4). Lanes 5-7, LN/splenocytes from ASMEL treated mice depleted of CD4 (5), CD8 (6), or NK cells (7) and treated in vitro with ASMEL and B16 tumor lysate.

Intravenous ASMEL Cures Established B16 Melanomas 9 intravenous (i.v.) injections of the ASMEL cured 60% of mice bearing established B16 tumors (p<0.0001 compared to VSV-GFP) (FIG. 2A), but generated no therapy against TC2 tumors (not shown; Kottke et al., *Nature Med.*, 17:854-859 (2011)) and therapy was lost in immunodeficient mice. Depletion of CD4+ T cells significantly decreased therapy (p=0.0005, depleted compared to non-depleted) (FIG. 2A), although CD4-depleted, ASMEL treatment was still significantly better than i.v. VSV-GFP (p=0.022) (FIG. 2A). There was no significant difference between mock depleted mice and CD8+ T cell-depleted mice upon treatment with the ASMEL (p=0.11) (FIG. 2A).

To test for the role of immune reactivity against xenogenic, as opposed to tissue specific, antigens in the ASMEL, the therapeutic efficacy of a VSV-expressed cDNA library from mouse melanoma (B16; Kottke et al., *Nature Med.*, 17:854-859 (2011)) (no xenogeneic, or altered self, antigens) (SMEL, Self Epitope Melanoma Library) was compared to that of the ASMEL (Altered Self Melanoma Epitope Library). Over two experiments, mice vaccinated with the ASMEL survived significantly longer than those treated with the SMEL (p=0.01), although SMEL treated mice survived significantly longer than mice treated with VSV-GFP (p=0.001).

Figure 2B:
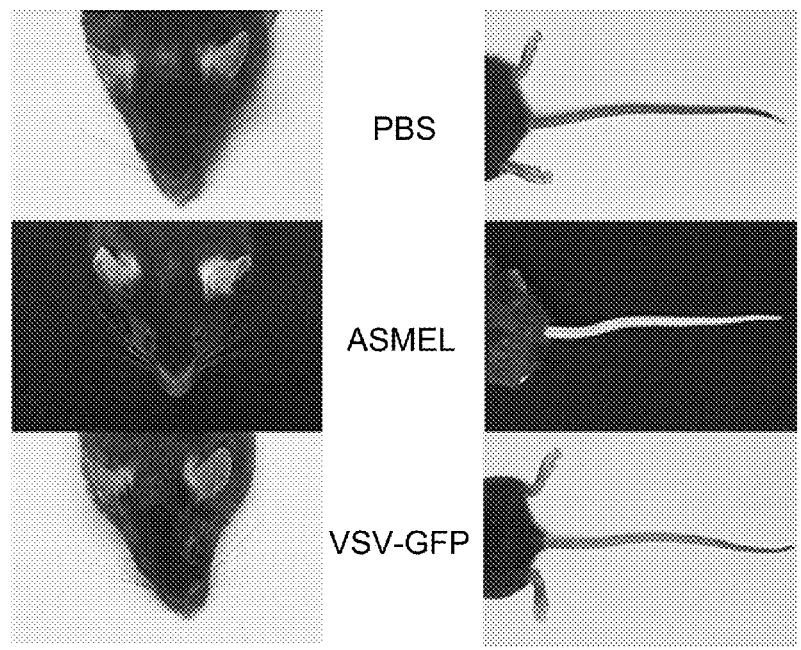
Figure 2C:
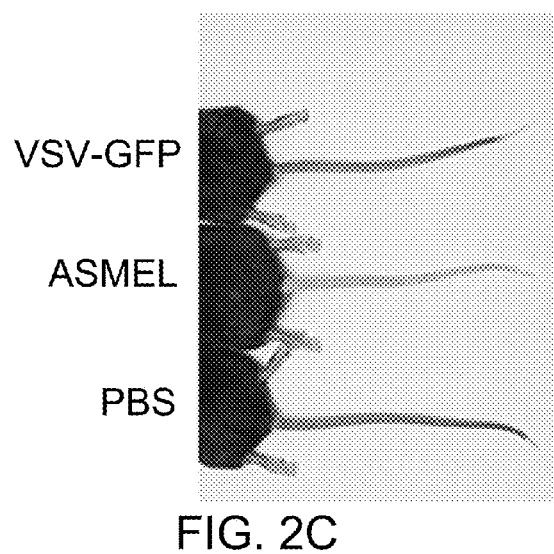

Mice cured by 9 i.v. injections of ASMEL did not develop detectable autoimmunity for 6 months following treatment. Thereafter, however, moderate symptoms were observed in 100% of treated mice, manifested as whitening of the whiskers (FIG. 2B) and tails (FIGS. 2B and 2C). Up to 12 months following injection of ASMEL, no mice developed any hair de-pigmentation significantly different to that of control mice injected with PBS (FIG. 2B). The mild autoimmunity seen in mice at 12 months (FIGS. 2B and 2C) progressed only marginally by 18 months post treatment (further whitening of tails and whiskers). No reproducible abnormal immune infiltration or tissue destruction was detected histologically, and there were no other obvious signs of autoimmunity. Splenocytes of mice 18 months post-treatment did not secrete IFN-γ in response to stimulation by B16 lysates or melanoma-associated epitopes.

ASMEL Primes a Tumor Specific IL-17 Response

Figure 2D:
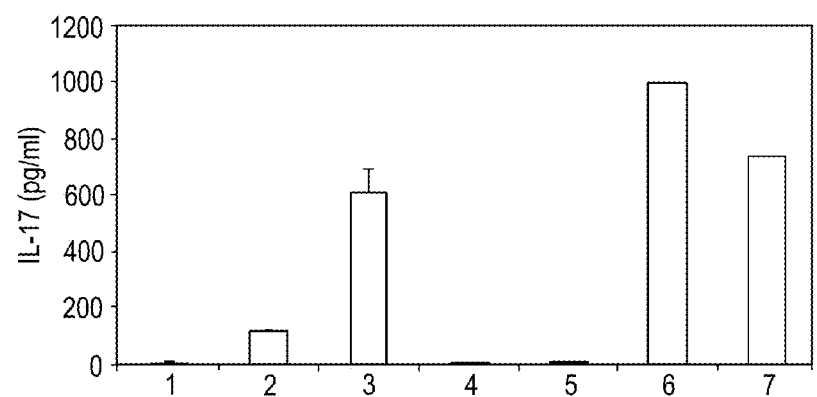

Pooled lymph node (LN) cells and splenocytes from ASMEL cured mice did not secrete IFN-γ, IL-4, IL-6, or IL-10 upon re-stimulation with B16 cell lysates in vitro either with, or without, infection/re-stimulation with the ASMEL (not shown). In contrast, LN/splenocytes from ASMEL cured mice secreted low levels of IL-17 upon re-stimulation with B16 (FIG. 2D, lanes 2 and 3), but not lysates from normal mouse prostate, pancreas (not shown), or TC2 prostate tumor lysates (FIG. 2D, lane 4). Levels of IL-17 were significantly increased by re-stimulation with ASMEL at an MOI of 10 (FIG. 2D, lane 3). However, MOI of 1, or lower, were ineffective at stimulating IL-17 secretion.

The ability of LN/splenocytes from ASMEL treated, immune subset depleted mice to secrete IL-17 when infected with the ASMEL and re-stimulated with B16 lysates (FIG. 2C, lanes 5-7) correlated with therapy of the ASMEL against B16 tumors (FIG. 2A).

Low MOI Induction of Recall IL-17 Responses is Mediated by Hsp70

Figures 3C, 3D:
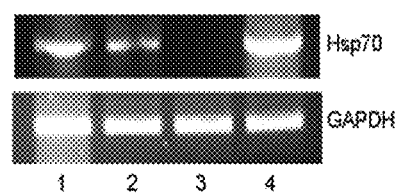
FIG. 3. VSV acts as an hsp70-mediated adjuvant. A. Expression of hsp70 was assayed by rtPCR from cDNA prepared from pooled LN and splenocytes ($10^4$/well) of C57BL/6 mice 24 hours following infection with either VSV-GFP or ASMEL at increasing MOI as shown. B. Expression of hsp70 by rtPCR from pooled LN and splenocytes ($10^4$/well) of C57BL/6 mice at 24, 36, or 48 hours following infection with either VSV-ova, VSV-GFP, or ASMEL at MOI 10. C. Pooled LN and splenocytes ($10^4$/well) from mice treated with 9 intravenous injections of ASMEL were infected 24 hours later with ASMEL or VSV-GFP at different MOI as shown and either in the presence, or absence, of added recombinant hsp70 (10 μg/mL). 24 hours later, representative wells were assayed by rtPCR for hsp70 expression ('Hsp70 Induction'; + positive signal; −, no detectable signal by rtPCR). Similarly treated triplicate wells were replenished with an additional $10^4$ LN/splenocytes and re-treated with a further round of virus infection 24 hours later. 48 hours following this final infection with virus, cultures were stimulated with melanoma B16 cell lysates and 48 hours later supernatants were assayed for IL-17 by ELISA. +, >200 pg/mL IL-17; ++, 200-400 pg/mL IL-17; +++>500 pg/mL IL-17. D. Expression of hsp70 was assayed by rtPCR from cDNA prepared from pooled LN and splenocytes ($10^4$/well) of TLR7$^{-/-}$ (lane 1), MyD88$^{-/-}$ (2), TLR4$^{-/-}$ (3) or C57BL/6 (4) mice 24 hours following infection with ASMEL at an MOI 10. E. Pooled LN and splenocytes ($10^4$/well) from C57BL/6, MyD88$^{-/-}$, TLR4$^{-/-}$, or TLR7$^{-/-}$ mice treated with 9 intravenous injections of ASMEL were infected 24 hours later with ASMEL at an MOI 10 either in the absence (−rhsp70), or presence (+rhsp70), of added recombinant hsp70 (10 μg/mL). 24 hours later, representative wells were assayed by rtPCR for hsp70 expression ('Hsp70 Induction'; +++, +, − rtPCR signal relative to that from C57BL/6 LN/splenocytes). Similarly treated triplicate wells were replenished with an additional $10^4$ LN/splenocytes and re-infected with a further round of virus infection 24 hours later. 48 hours following this final infection with virus, cultures were stimulated with melanoma B16 cell lysates, and 48 hours later supernatants were assayed for IL-17 by ELISA. +, >200 pg/mL IL-17; ++, 200-400 pg/mL IL-17; +++>500 pg/mL IL-17.

To detect individual VSV encoding specific cDNA which stimulate anti-tumor IL-17 responses, it was determined to be preferable to increase the sensitivity of this recall response from LN/splenocytes when infected in vitro with the ASMEL at MOI lower than 10. hsp70 was induced within 24 hours by infection of ASMEL-treated LN/splenocytes with high, but not low (<10), MOI of VSV (FIG. 3A). hsp70 induction was independent of whether the VSV transgene was only GFP, or multiple different inserts (cDNA) (FIG. 3A). However, prolonged hsp70 expression was only observed with VSV expressing multiple cDNA, as opposed to only ova or GFP (FIG. 3B). Therefore, (a) the MOI of VSV infection correlated with induction of hsp70, and (b) detection of a tumor-specific recall IL-17 response (>200 pg/mL) (FIGS. 2 and 3C) required both a range of VSV-expressed cDNA molecules and was associated with hsp70. Therefore, by supplying exogenous hsp70 to LN/splenocyte cultures, it was hypothesized to be possible to detect recall IL-17 responses to ASMEL containing viruses at lower (<10) MOI. Consistent with this hypothesis, LN/splenocyte cultures from ASMEL-treated mice secreted IL-17 in response to re-stimulation with B16 (but not TC2) lysate when infected with the ASMEL (but not VSV-GFP) virus at MOI of 1.0 or lower in the presence of recombinant hsp70 (FIG. 3C).

Induction of hsp70 following infection of LN/splenocyte cultures with ASMEL depended upon TLR4- (FIG. 3D), but not upon MyD88- or TLR7-, signaling (FIG. 3E). Although IL-17 secretion required signaling by TLR4, TLR7, and MyD88 (FIG. 3E), it could be rescued by addition of rhsp70 in the absence of MyD88 or TLR4 signaling.

Identifying VSV-cDNA Viruses that Induce Tumor Specific IL-17 Memory Responses

This hsp70-enhanced in vitro assay was used to screen for individual viruses within the ASMEL stocks that induced tumor-specific IL-17 recall responses as described in FIG. 6A. Individual VSV-cDNA viruses were cloned by limiting dilution of sequentially diluted, and screened, aliquots of the ASMEL virus stock that induced IL-17 at levels significantly above background (>100 pg/mL) (FIGS. 6A and 6B). Viruses recovered from 24 'single pfu'-containing wells (FIG. 6A) were screened by PCR for their encoded cDNA inserts (FIG. 6C). Seven viruses encoded 5' coding sequences of the human N-RAS oncogene; six were identical, containing 555 bp of the 5' coding region whilst one virus contained 444 bp of the same sequence. Codon 13 of all seven viruses contained a G-T mutation compared to the wild type sequence but all the remaining sequences contained no mutations (Hall and Brown, *Nucleic Acids Res.*, 13:5255-5268 (1985)). Four viruses encoded un-mutated sequences of the 5' end of the human TYRP1 gene (Shibata et al., *Biochem. Biophys. Res. Commun.*, 184:568-575 (1992)); three of these contained 1260 bp of hTYRP1 sequence, and a fourth virus contained 1199 bp (Shibata et al., *Biochem. Biophys. Res. Commun.*, 184:568-575 (1992)). Two identical viruses were recovered that encoded sequence of the human cytochrome C1 gene, with a G-A mutation at position 1 compared to the published sequence (Suzuki et al., *J. Biol. Chem.*, 264:1368-1374 (1989)). A single virus encoded the 5' end of the human TRIM 33 gene. The remaining viruses had no interpretable sequences.

In Vitro Validation of VSV-Encoded Tumor Antigens

Figure 4A:
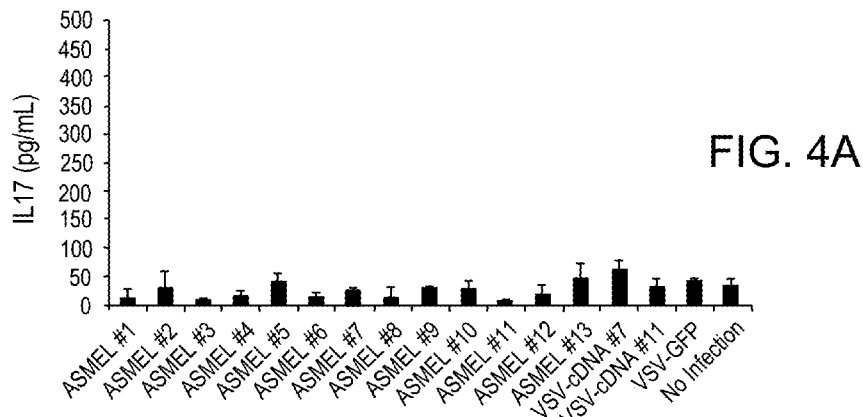
FIG. 4. VSV-induced TGF-β masks the tumor specific IL-17 recall response. A and B. LN/splenocyte cultures from ASMEL-vaccinated mice were screened for IL-17 (A) or TGF-β (B) secretion following infection with 12 single viruses purified by limiting dilution from the parental, unselected ASMEL stock (ASMEL#1-#12), with representative viruses selected from the screen shown in FIG. 6—VSV-cDNA clone #3 (encoding N-RAS sequences), VSV-cDNA clone #7 (encoding TYRP1 sequences), VSV-cDNA clone #11 (encoding CYT-C sequences)—or with VSV-GFP (all infections at MOI 10). C. The IL-17 screening assay of A above was repeated but in the presence of TGF-β Rh Fc Chimera to inhibit TGF-β in the cultures.
Figure 4B:
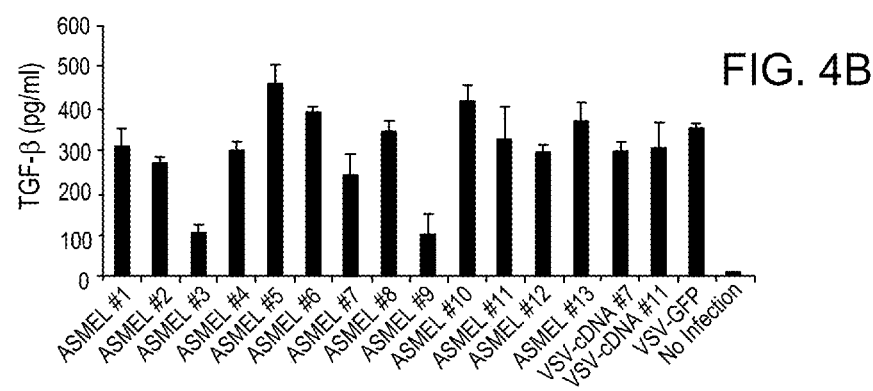
Figure 4C:
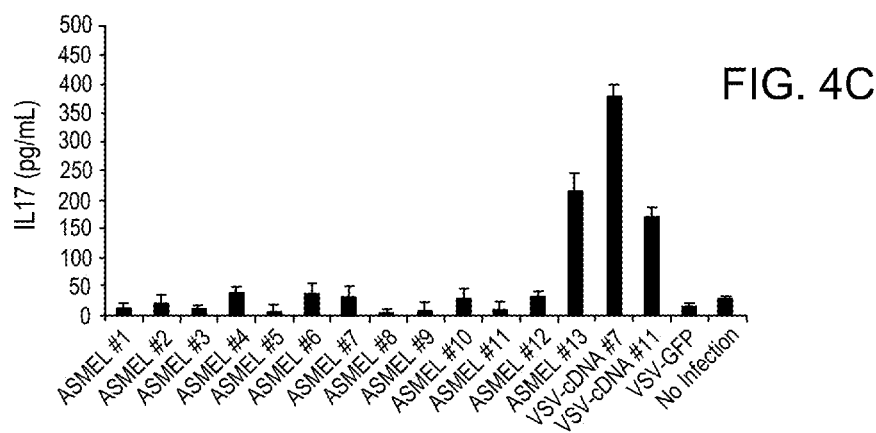

To validate these four separately derived cDNA sequences as potential tumor associated antigens, one virus from each group with the longest encoded sequence of each gene (VSV-N-RAS clone #3, -TYRP1 clone #7, -CYT-C clone #11, or -TRIM33 clone #12) was expanded in BHK cells. In addition, 12 single viruses were purified by limiting dilution from the parental, unselected ASMEL stock (ASMEL#1-#12). None of the randomly selected viruses ASMEL #1-#12 induced IL-17 following infection of LN/splenocyte cultures from ASMEL-vaccinated mice, even at high MOI (FIG. 4A). Surprisingly, neither did any of the four selected viruses (VSV-N-RAS, -TYRP1, -CYT-C or -TRIM33) (FIG. 4A). VSV induces potent suppressor activities in vivo as described elsewhere (Willmon et al., *Mol. Ther.*, 19:140-149 (2010)). Infection of the LN/splenocyte cultures induced high levels of TGF-β, independent of the nature of the cDNA insert in the virus (FIG. 4B). When LN/splenocyte cultures were infected with either the VSV-N-RAS, VSV-TYRP1, or VSV-CYT-C viruses (but not the VSV-TRIM33 virus), in the presence of TGF-β blockade (Willmon et al., *Mol. Ther.*, 19:140-149 (2010)), significant levels of IL-17 were induced (FIG. 4C). In contrast, none of the randomly cloned viruses (ASMEL #1-#12) induced IL-17 even in the presence of TGF-β blockade (FIG. 4C).

In Vivo Validation of VSV-Encoded Tumor Antigens

A three way combination of the VSV-N-RAS, VSV-TYRP1, and VSV-CYT-C viruses was sufficient to overcome VSV-induced TGF-β-dependent suppression (Willmon et al., *Mol. Ther.*, 19:140-149 (2010)) and induced significant levels of IL-17 even without TGF-β blockade (FIG. 5A). Blockade of TGF-β further increased levels of IL-17 with the combination (FIG. 5B). The ability of VSV-cDNA viruses to induce IL-17 in combination depended on the nature of the cDNA insert since combining three different non-selected viruses (ASMEL #1, #2 and #3) or (ASMEL #4, #5, and #6) did not induce IL-17, even with TGF-β blockade (FIG. 5B).

It was tested whether any of the viruses could prime an anti-B16 response in naive LN/splenocyte cultures, as opposed to stimulating a recall response from previously treated mice. Neither the randomly cloned VSV-cDNA (not shown), nor the selected viruses (FIG. 5C), induced either IFN-γ (not shown) or IL-17 (FIG. 5C) from repeatedly infected LN/splenocytes from naive C57BL/6 mice in the absence of TGF-β blockade (FIG. 5C). Two way combinations were also ineffective (FIG. 5C). In contrast, a combination of the VSV-N-RAS, VSV-TYRP1, and VSV-CYT-C viruses induced significant levels of IL-17 in response to B16 lysates (FIG. 5C), but not TC2 prostate lysates (not shown), to levels of about 60% of those induced by the un-fractionated ASMEL stock (FIG. 5C). VSV-TRIM33 alone, in double combination, or along with any two of the other viruses, did not induce IL-17 (FIG. 5C), although inclusion of VSV-TRIM33 with the three other viruses did not significantly inhibit IL-17 production (FIG. 5C).

The VSV-N-RAS, VSV-TYRP1, and VSV-CYT-C viruses alone, in double combinations, and in triple combinations were tested for the ability to treat established B16 melanomas in vivo. VSV expressing the foreign, non-self, tumor associated ova antigen can induce tumor rejection in a proportion of mice bearing B16ova tumors (Diaz et al., *Cancer Res.*, 67:2840-2848 (2007)). However, VSV expressing self, or near-self, tumor antigens such as TRP-2 or gp100, did not induce significant therapy against B16 tumors (FIG. 5D), even though splenocytes from these treated mice did secrete IFN-γ, but not IL-17, when re-stimulated with B16 tumor lysates or their cognate antigens in vitro (not shown; Wongthida et al., *Mol. Ther.*, 19:150-158 (2011)). None of the individual VSV-N-RAS, VSV-TYRP1, and VSV-CYT-C viruses had any significant therapy against established B16 melanomas compared to PBS or VSV-GFP-treated controls (not shown). Also consistent with the in vitro data, double combinations of these viruses gave no therapy (FIG. 5E). However, using the same total dose of virus administration, a combination of the three different VSV-N-RAS, VSV-TYRP1, and VSV-CYT-C viruses generated highly significant therapy compared to any of the control, or double combination treatments, with up to 60% of mice being cured long term (FIG. 5E). In addition, prophylactic vaccination (days −7, −6, and −5 before s.c. B16 challenge) with either the intact ASMEL ($10^7$ pfu/injection), or with the same total dose of virus containing the combination of VSV-cDNA clone#3 (N-RAS)+clone#7 (TYRP1)+clone#11 (CYT-C), completely prevented tumor growth in 6/7 and 8/8 mice. In contrast, all mice vaccinated with VSV-GFP developed progressively growing tumors reaching a diameter of 1.0 cm by day 25.

Taken together, these results demonstrate that viral expressed cDNA libraries are effective against melanoma and that an altered self-library derived from tumor cells (as opposed to normal cells) can be used effectively against established tumors with limited autoimmunity (FIGS. 1 and 2). For example, results with the ASMEL and SMEL indicate that a cDNA library from a xenogeneic, altered-self source (human in the mouse context) can have additional adjuvant properties compared to a library from an autologous self-source (mouse in mouse). This adjuvant-like effect can derive partly from altered self-versions of self-antigens in the xenogeneic library, which increases the immunogenicity of relevant epitopes. In addition, FIGS. 2A and 2D demonstrate that the immune reactivity generated is not simply directed against xenoantigens corresponding to normal household polypeptide.

These results also demonstrate the development of an in vitro screen based upon the ability of LN/splenocytes from ASMEL treated mice to present tumor-associated epitopes from the ASMEL upon in vitro infection/stimulation to memory IL-17 $CD4^+$ T cells, which then secreted IL-17 in response to melanoma, but not prostate, tumor lysates (FIG. 2). Consistent with the involvement of hsp70 as an adjuvant for breaking tolerance, this response can be mediated by a TLR-4-dependent, VSV-mediated induction of hsp70 with subsequent MyD88-, and TLR-7, dependent signaling of IL-17 secretion by hsp70 (FIG. 3). The tumor specific IL-17 memory response could be induced by infection as low as an MOI of ~1 by addition of exogenous hsp70 (FIG. 3). Using this in vitro assay, single VSV with cDNA inserts from coding sequences of N-RAS, TYRP1, CYT-C and TRIM33 were isolated (FIG. 6). Surprisingly, none of these viruses alone induced B16-specific IL-17 recall responses in vitro (FIG. 4A), unless VSV-induced TGF-β was blocked (FIG. 4C). However, combination of the N-RAS, TYRP1, CYT-C viruses overcame TGF-β mediated suppression of the IL-17 recall response, even without TGF-β blockade (FIG. 5A). Significantly, these three viruses together also primed a de novo tumor specific IL-17 response from LN/splenocytes of naïve C57BL/6 mice (FIGS. 5A and 5C), although levels of IL-17 only reached about 60% of those induced by infection with the un-fractionated ASMEL (FIG. 5C). Autoimmunity (FIG. 2) was very mild and progresses very slowly, if at all, beyond 12 months. Therefore, infection with the ASMEL may generate anti-tumor effector responses that are suppressed in the long term by VSV-mediated induction of suppressor mechanisms, thereby limiting the development of autoimmunity.

Consistent with the in vitro data, therapy against B16 tumors was reconstituted in vivo only when the three VSV-N-RAS, VSV-TYRP1, and VSV-CYT-C viruses were used in triple combination (FIG. 5E). Therefore, these results demonstrate that only certain self, or near self, cDNAs can induce CD4-dependent, melanoma-specific IL-17 responses that cumulatively translate into CD4-dependent anti-tumor therapy. cDNA encoding parts of the N-RAS, TYRP1, and CYT-C genes have this property, and can, therefore, be regarded as tumor antigens. Since all the N-RAS-encoding VSV-cDNA encoded a RAS peptide with a mutated codon 13, it is possible that this insert represents a class of tumor specific epitopes.

Combining three VSV-cDNAs from the ASMEL library induced about 60% of the IL-17 recall response from LN/splenocyte cultures (FIG. 5C) and generated therapy similar to, or less than, that generated by the ASMEL (FIG. 5E). Therefore, it seems probable that the unselected ASMEL contains additional active components, lacking from the triple combination, that contribute to therapy. These may either be additional antigenic cDNAs or adjuvant properties.

An issue for clinical translation of these studies is whether cDNA sourced from a xenogeneic, normal cell type is more, or less, efficacious against tumors than is VSV-cDNA derived from a xenogeneic, tumor source. From studies in the prostate model (Kottke et al., *Nature Med.*, 17:854-859 (2011)), it is clear that the cDNA library does not have to come from tumor tissue and that VSV-cDNA from normal cells of the same histological type is effective against established tumors. It is possible that a library from normal cells will incorporate a greater range of antigens against which tolerance might be broken for tumor rejection than will a library from tumor cells, since certain antigens may have been lost during in vivo evolution of the tumor cells under immune pressure. In addition, the data from the prostate model clearly demonstrate that a xenogeneic (human) library is immunologically superior (in terms of generating rejection of (murine) tumors) to a fully self (murine) library from the normal tissue when presented in the context of the VSV platform. Therefore, in the human clinical context, a VSV-expressed cDNA library derived from a xenogeneic melanocyte cell source would be at least as effective, if not more so, than a human tumor cDNA library.

In summary, the results provided herein demonstrate the development of technology that can be used to identify arrays of self, or near self, tumor associated antigens that act optimally in combination to signal T cell activation and tumor rejection. This technology can be applicable for the treatment of a wide variety of cancer types. In addition, it can permit the cloning of antigens which, alone, may not be identified as tumor associated antigens, but which, when acting as one component of an array of different antigens, can be involved in generating optimal anti-tumor immunity. The success of VSV-expressed cDNA libraries in identifying these arrays of antigens can be based on at least three properties. Thus, the immunogenicity of antigen presentation through viral-associated gene expression can induce potent T cell responses against the tumor associated antigens. Second, use of the cDNA library can allow a large number of potential tumor associated antigens to be surveyed by the immune system. Finally, the broad tropism of the virus can allow for delivery in vivo of this large repertoire of potential tumor associated antigens to a wide range of different types of APC. Therefore, this technology can allow identification of a series of individually clinically relevant epitopes that, when expressed combinatorially from an appropriate viral platform, can collectively be used to construct a translational pipeline of viral vaccines with a safe, but effective, therapeutic index.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for identifying, from a second nucleic acid library, a nucleic acid encoding an antigen having the ability, in combination with at least two other antigens, to stimulate an anti-cancer response, wherein said second nucleic acid library is a library of virally-expressed nucleic acid members and has the ability to stimulate an anti-cancer response when administered to a mammal having cancer, wherein said method comprises:
   (a) contacting immune cells with an aliquot of said second nucleic acid library to form a collection of virally infected cells, wherein said immune cells were obtained from a mammal that exhibited a reduction in the number of cancer cells following administration of a first nucleic acid library,
   (b) obtaining a cell from said collection of virally infected cells that secretes an IL-17 polypeptide, wherein said cell contains a nucleic acid member of said second nucleic acid library, and
   (c) determining the sequence of said nucleic acid member of said cell, wherein said nucleic acid member is said nucleic acid encoding an antigen having the ability, in combination with at least two other antigens, to stimulate an anti-cancer response.

2. The method of claim 1, wherein said second nucleic acid library is a cDNA library.

3. The method of claim 1, wherein said second nucleic acid library is a VSV-expressed cDNA library.

4. The method of claim 1, wherein said first nucleic acid library is a cDNA library.

5. The method of claim 1, wherein said first nucleic acid library is a VSV-expressed cDNA library or an expressed cDNA library via another virus, animal cell, bacterial cell, or fungus.

6. The method of claim 1, wherein said second nucleic acid library and said first nucleic acid library are the same library.

7. The method of claim 1, wherein said immune cells are lymph node cells and splenocytes.

8. The method of claim 1, wherein said contacting step (a) comprises contacting said immune cells with said aliquot in the presence of an hsp70 polypeptide.

9. The method of claim 8, wherein said hsp70 polypeptide is a human hsp70 polypeptide.

10. The method of claim 1, wherein said aliquot comprises a multiplicity of infection (MOI) of less than 10.

11. The method of claim 1, wherein said mammal is a rodent or primate.

12. The method of claim 1, wherein said mammal is a mouse.

13. The method of claim 1, wherein said mammal is a human.

* * * * *

SEQUENCE LISTING

<160> NUMBER OF SEQ ID NOS: 12

<210> SEQ ID NO 1
<211> LENGTH: 46
<212> TYPE: DNA
<213> ORGANISM: Homo sapiens

<400> SEQUENCE: 1
atgactgagt acaaactggt ggtggtggag caggtgttgt tgggaa         46

<210> SEQ ID NO 2
<211> LENGTH: 42
<212> TYPE: DNA
<213> ORGANISM: Homo sapiens

<400> SEQUENCE: 2
aacagcagtg atgatgggac tcagggttgt atgggattgc ca             42

<210> SEQ ID NO 3
<211> LENGTH: 39
<212> TYPE: DNA
<213> ORGANISM: Homo sapiens

<400> SEQUENCE: 3
atgactgagt acaaactggt ggtggttgga gcaggtgtt                 39

<210> SEQ ID NO 4
<211> LENGTH: 23
<212> TYPE: DNA
<213> ORGANISM: Homo sapiens

<400> SEQUENCE: 4
tcattgaaac ctcagccaag acc                                  23

<210> SEQ ID NO 5
<211> LENGTH: 46
<212> TYPE: DNA
<213> ORGANISM: Homo sapiens

<400> SEQUENCE: 5
atgagtgctc ctaaactcct ctctctgggc tgtatcttct tcccct         46

<210> SEQ ID NO 6
<211> LENGTH: 39
<212> TYPE: DNA
<213> ORGANISM: Homo sapiens

<400> SEQUENCE: 6
atgcagtctt tgatgaatgg ctgaggagat acaatgctg                 39

<210> SEQ ID NO 7
<211> LENGTH: 36
<212> TYPE: DNA
<213> ORGANISM: Homo sapiens

<400> SEQUENCE: 7
atgagtgctc ctaaactcct ctctctgggc tgtatc                    36

<210> SEQ ID NO 8
<211> LENGTH: 44
<212> TYPE: DNA
<213> ORGANISM: Homo sapiens

<400> SEQUENCE: 8

```
gaacaggggg acaaacccat tgtctccaa atgatcctat tttt            44
```

<210> SEQ ID NO 9
<211> LENGTH: 60
<212> TYPE: DNA
<213> ORGANISM: Homo sapiens

<400> SEQUENCE: 9

```
atggaggttc aagacggccc caatgaagat ggggagatgt tcatgcggcc agggaagctg    60
```

<210> SEQ ID NO 10
<211> LENGTH: 39
<212> TYPE: DNA
<213> ORGANISM: Homo sapiens

<400> SEQUENCE: 10

```
gcattgcccc ctgacctcag ctacatcgtg cgagctagg            39
```

<210> SEQ ID NO 11
<211> LENGTH: 9
<212> TYPE: PRT
<213> ORGANISM: Artificial Sequence
<220> FEATURE:
<223> OTHER INFORMATION: synthetic polypeptide

<400> SEQUENCE: 11

```
Lys Val Pro Arg Asn Gln Asp Trp Leu
1               5
```

<210> SEQ ID NO 12
<211> LENGTH: 8
<212> TYPE: PRT
<213> ORGANISM: Artificial Sequence
<220> FEATURE:
<223> OTHER INFORMATION: synthetic polypeptide

<400> SEQUENCE: 12

```
Ser Ile Ile Asn Phe Glu Lys Leu
1               5
```